(12) United States Patent
Fujii et al.

(10) Patent No.: US 8,765,171 B2
(45) Date of Patent: Jul. 1, 2014

(54) METHODS AND COMPOSITIONS FOR LIPOSOMAL FORMULATION OF ANTIGENS AND USES THEREOF

(75) Inventors: Gary Fujii, Rancho Palos Verdes, CA (US); Francis C. Szoka, Jr., San Francisco, CA (US); Douglas S. Watson, Harrisonburg, VA (US)

(73) Assignees: The Regents of the University of California, Oakland, CA (US); Molecular Express, Inc., Rancho Dominquez, CA (US)

( * ) Notice: Subject to any disclaimer, the term of this patent is extended or adjusted under 35 U.S.C. 154(b) by 899 days.

(21) Appl. No.: 12/720,592

(22) Filed: Mar. 9, 2010

(65) Prior Publication Data
US 2010/0226973 A1    Sep. 9, 2010

Related U.S. Application Data

(60) Provisional application No. 61/158,694, filed on Mar. 9, 2009.

(51) Int. Cl.
*A61K 9/127* (2006.01)
*A61K 39/00* (2006.01)
*A61K 39/385* (2006.01)
*C07J 9/00* (2006.01)
*A61P 37/04* (2006.01)

(52) U.S. Cl.
USPC .............. 424/450; 424/184.1; 424/194.1; 552/544

(58) Field of Classification Search
None
See application file for complete search history.

(56) References Cited

U.S. PATENT DOCUMENTS

| | | | |
|---|---|---|---|
| 5,004,737 A | 4/1991 | Kim et al. | |
| 5,169,933 A * | 12/1992 | Anderson et al. | 530/391.3 |
| 5,643,575 A | 7/1997 | Martinez et al. | |
| 5,672,662 A | 9/1997 | Harris et al. | |
| 5,705,153 A | 1/1998 | Shorr et al. | |
| 5,730,990 A | 3/1998 | Greenwald et al. | |
| 5,817,334 A * | 10/1998 | Schmidt et al. | 424/450 |
| 5,902,588 A | 5/1999 | Greenwald et al. | |
| 5,932,462 A | 8/1999 | Harris et al. | |
| 6,057,091 A | 5/2000 | Beachy et al. | |
| 7,312,206 B2 | 12/2007 | Panzner et al. | |
| 2002/0018808 A1 | 2/2002 | Alving et al. | |
| 2005/0169979 A1 | 8/2005 | Michaeli et al. | |
| 2005/0244420 A1 | 11/2005 | Soni et al. | |
| 2008/0207487 A1* | 8/2008 | DeFrees et al. | 514/2 |

FOREIGN PATENT DOCUMENTS

| | | |
|---|---|---|
| WO | 9014837 | 12/1990 |
| WO | 9219265 | 11/1992 |
| WO | 9313202 | 7/1993 |
| WO | 0075165 | 12/2000 |
| WO | 02/066490 | 8/2002 |

OTHER PUBLICATIONS

Makino et al., Molecular Characterization and Protein Analysis of the cap Region, Which Is Essential for Encapsulation in *Bacillus anthracis*, Journal of Bacteriology, Feb. 1989;171(2):722-730.
Marusic et al., Chimeric Plant Virus Particles as Immunogens for Inducing Murine and Human Immune Responses against Human Immunodeficiency Virus Type 1, Journal of Virology, 2001; 75(18):8434-8439.
Matsumoto Sachio et al., Preparation of Lipid Vesicles on the Basis of a Technique for Providing W/O/W Emulsions, Journal of Colloid and Interface Science, 1977; 62(1): 149-157.
Matyas Gary R. et al., Lipid binding properties of 4E10, 2F5, and WR304 monoclonal antibodies that neutralize HIV-1, Biochimica et Biophysica Acta, 2009; 1788:660-665.
McGee et al., The encapsulation of a model protein in poly (D, L lactide-co-glycolide) microparticles of various sizes: an evaluation of process reproducibility, J. Microencapsulation, 1997; 14(2): 197-210.
Mesnage et al., The Capsule and S-Layer: Two Independent and Yet Compatible Macromolecular Structures in *Bacillus anthracis*, Journal of Bacteriology, Jan. 1998;180(1):52-58.
Miller et al., LPS, TLR4 and Infectious Disease Diversity, Nature Reviews Microbiology, 2005; 3(1):36-46.
Montero et al., The Membrane-Proximal External Region of the Human Immunodeficiency Virus Type 1 Envelope: Dominant Site of Antibody Neutralization and Target for Vaccine Design, Microbiology and Molecular Biology Reviews, Mar. 2008; 72(1):54-85.
Muster et al., Cross-neutralizing activity against divergent human immunodeficiency virus type 1 isolates induced by the gp41 sequence ELDKWAS, Journal of Virology, 1994; 68(6):4031-4034.
Ofek et al., Structure and Mechanistic Analysis of the Anti-Human Immunodeficiency Virus Type 1 Antibody 2F5 in Complex with Its gp41 Epitope, Journal of Virology, 2004; 78(19):10724-10737.
Olson et al., Preparation of Liposomes of Defined Size Distribution by Extrusion Through Polycarbonate Membranes, Biochimica et Biophysica Acta, 1979; 557: 9-23.
Penn-Nicholson et al., Assessment of antibody responses against gp41 in HIV-1-infected patients using soluble gp41 fusion proteins and peptides derived from M group consensus envelope, Virology, 2008;372(2):442-456.
Pick Uri; Liposomes with a Large Trapping Capacity Prepared by Freezing and Thawing of Sonicated Phospholipid Mixtures, Archives of Biochemistry and Biophysics,1981; 212(1):186-194.

(Continued)

*Primary Examiner* — Shanon A Foley
(74) *Attorney, Agent, or Firm* — Michael A. Whittaker; Acuity Law Group, P.C.

(57) ABSTRACT

The present invention relates to liposomal vaccine compositions, methods for the manufacture thereof, and methods for the use thereof to stimulate an immune response in an animal. These compositions comprise dimyristoylphosphatidylcholine ("DMPC"); either dimyristoylphosphatidylglycerol ("DMPG") or dimyristoyltrimethylammonium propane ("DMTAP") or both DMPC and DMTAP; and at least one sterol derivative providing a covalent anchor for one or more immunogenic polypeptide(s) or carbohydrate(s).

21 Claims, 9 Drawing Sheets

(56) References Cited

OTHER PUBLICATIONS

Razin Shmuel, Reconstitution of Biological Membranes, Biochimica et Biophysica Acta, 1972; 265:241-296.
Robinson et al., Palmitic acid conjugation of a protein antigen enhances major histocompatibility complex class II-restricted presentation to T cells, Immunology, 1992; 76(4):593-598.
Salzwedel et al., A Conserved Tryptophan-Rich Motif in the Membrane-Proximal Region of the Human Immunodeficiency Virus Type 1 gp41 Ectodomain Is Important for Env-Mediated Fusion and Virus Infectivity, Journal of Virology 1999; 73(3):2469-2480.
Sathaliyawala et al., Assembly of Human Immunodeficiency Virus (HIV) Antigens on Bacteriophage T4: a Novel In Vitro Approach to Construct Multicomponent HIV Vaccines, Journal of Virology, 2006;80(15):7688-7698.
Schibli et al., The Membrane-Proximal Tryptophan-Rich Region of the HIV Glycoprotein, gp41, Forms a Well-Defined Helix in Dodecylphosphocholine Micelles, Biochemistry, 2001; 40: 9570-9578.
Schieren et al., Comparison of Large Unilamellar Vesicles Prepared by a Petroleum Ether Vaporization Method With Multilamellar Vesicles, Biochimica et Biophysica Acta, 1978; 542: 137-153.
Schuster et al., Production of Antibodies Against Phosphocholine, Phosphatidylcholine, Sphingomyelin, and Lipid A by Injection of Liposomes Containing Lipid A, Journal of Immunology, 1979;122(3):900-905.
Szoka, Jr. et al., Procedure for preparation of liposomes with large internal aqueous space and high capture by reverse-phase evaporation, Proc. Natl. Acad. Sci. USA, 1978; 75(9):4194-4198.
Taylor et al., Structure-Function Analysis of Proteins through the Design, Synthesis, and Study of Peptide Models, Methods in Enzymology, 1987; 154:473-498.
Topchieva et al., Synthesis and Physicochemical Properties of Protein Conjugates with Water-Soluble Poly(alkylene oxides), Bioconjugate Chem., 1995; 6: 380-388.
Vcelar et al., Reassessment of autoreactivity of the broadly neutralizing HIV antibodies 4E10 and 2F5 and retrospective analysis of clinical safety data, AIDS, 2007; 21(16):2161-2170.
Verma et al., Adjuvant Effects of Liposomes Containing Lipid A: Enhancement of Liposomal Antigen Presentation and Recruitment of Macrophages, Infection and Immunity, 1992; 60(6):2438-2444.
Watson et al., All-trans retinoic acid potentiates the antibody response in mice to a lipopeptide antigen adjuvanted with liposomal lipid A, Immunology and Cell Biology, 2009; 87, 630-633.
Watson et al., Role of lipid structure in the humoral immune response in mice to covalent lipid—peptides from the membrane proximal region of HIV-1 gp41, Vaccine, 2009; 27: 4672-4683.
White et al., Antibody and cytotoxic T-lymphocyte responses to a single liposome-associated peptide antigen, Vaccine, 1995; 13(12):1111-1122.
Ye et al., Antigenic properties of a transport-competent influenza HA/HIV Env chimeric protein, Virology, 2006;352 (1):74-85.
Yokochi et al., Retention of Bacterial Lipopolysaccharide at the Site of Subcutaneous Injection, Infection and Immunity, 1989;57(6):1786-1791.
Zhang et al., Induction of Mucosal and Systemic Neutralizing Antibodies against Human Immunodeficiency Virus Type 1 (HIV-1) by Oral Immunization with Bovine Papillomavirus-HIV-1 gp41 Chimeric Virus-Like Particles, Journal of Virology, 2004;78(15):8342-8348.
Zwick et al., Broadly Neutralizing Antibodies Targeted to the Membrane-Proximal External Region of Human Immunodeficiency Virus Type 1 Glycoprotein gp41, Journal of Virology, 2001;75(22):10892-10905.
Sun et al., HIV-1 Broadly Neutralizing Antibody Extracts Its Epitope from a Kinked gp41 Ectodomain Region on the Viral Membrane, Immunity, vol. 28, Issue 1, 52-63, Jan. 18, 2008.
International Search Report and Written Opinion issued Apr. 16, 2010 by the ISA/US in PCT/US2010/026711, filed Mar. 9, 2010.

Alam et al., The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes, The Journal of Immunology, 2007;178(7):4424-4435.
Alamet et al., Human Immunodeficiency Virus Type 1 gp41 Antibodies That Mask Membrane Proximal Region Epitopes: Antibody Binding Kinetics, Induction, and Potential for Regulation in Acute Infection, Journal of Virology, 82 (1):115-125.
Alfsen et al., HIV-1 gp41 Envelope Residues 650-685 Exposed on Native Virus Act as a Lectin to Bind Epithelial Cell Galactosyl Ceramide*, The Journal of Biological Chemistry, 2002; 277(28):25649-25659.
Alving et al., Liposomes as Carriers of Peptide Antigens: Induction of Antibodies and Cytotoxic T Lymphocytes to Conjugated and Unconjugated Peptides, Immunologicall Reviews, 1995; 145:5-31.
Alving, Liposomes as carriers of antigens and adjuvants, Journal of Immunological Methods, 1991;140 (1): 1-13.
Alving et al., Lipid A and liposomes containing lipid A as antigens and adjuvants, Vaccine, 2008; 26(24): 3036-3045.
Banerji et al., Membrane Lipid Composition Modulates the Binding Specificity of a Monoclonal Antibody Against Liposomes, Biochimica et Biophysica Acta, 1982;689 (2): 319-326.
Banerji et al., Antibodies Against Liposomes in Normal and Immune-Defective Mice, The Journal of Immunology, 1982;128(4):1603-1607.
Batzri et al., Single bilayer liposomes prepared without sonication, Biochimica et Biophysica Acta, 1973; 298:1015-1019.
Beck et al., Membrane-specific antibodies induced by liposomes can simultaneously bind to HIV-1 protein, peptide, and membrane lipid epitopes; Journal of Drug Targeting, 2008; 16(7-8):535-542.
Biro et al., Novel anti-cholesterol monoclonal immunoglobulin G antibodies as probes and potential modulators of membrane raft-dependent immune functions, Journal of Lipid Research, 2007; 48(1):19-29.
Brown et al., Monoclonal Antibodies to Phosphatidylinositol Phosphate Neutralize Human Immunodeficiency Virus Type 1: Role of Phosphate-Binding Subsites, Journal of Virology, 2007; 81(4):2087-2091.
Brugger et al., The HIV lipidome: A raft with an unusual composition, Proceedings of the National Academy of Sciences (PNAS) 2006; 103(8):2641-2646.
Brunel et al., Structure-Function Analysis of the Epitope for 4E10, a Broadly Neutralizing Human Immunodeficiency Virus Type 1 Antibody, Journal of Virology, 2006; 80(4):1680-1687.
Cardoso et al., Broadly Neutralizing Anti-HIV Antibody 4E10 Recognizes a Helical Conformation of a Highly Conserved Fusion-Associated Motif in gp41, Immunity, 2005; 22(2):163-173.
Cardoso et al., Structural Basis of Enhanced Binding of Extended and Helically Constrained Peptide Epitopes of the Broadly Neutralizing HIV-1 Antibody 4E10, Journal of Molecular Biology 2007; 365(5):1533-1544.
Chabot J. et al., Anthrax capsule vaccine protects against experimental infection, Vaccine, 2004; 23:43-47.
Chan David C. et al., Core Structure of gp41 from the HIV Envelope Glycoprotein, Cell, 1997; 89(2): 263-273.
Chattopadhyay et al., Ionization, Partitioning, and Dynamics of Trytophan Octyl Ester: Implications for Membrane-Bound Tryptophan Residues, Biophysical Journal 1997; 73(2):839-849.
Coutant et al., Both lipid environment and pH are critical for determining physiological solution structure of 3-D-conserved epitopes of the HIV-1 gp41-MPER peptide P1, The FASEB Journal 2008; 22(12):4338-4351.
Dal Monte et al., Antigen presentation by B cells and macrophages of cytochrome c and its antigenic fragment when conjugated to the surface of liposomes, Vaccine 1989; 7(5):401-408.
Davis et al., Human Immunodeficiency Virus Type 2 (HIV-2)/HIV-1 Envelope Chimeras Detect High Titers of Broadly Reactive HIV-1 V3-Specific Antibodies in Human Plasma, Journal of Virology, 2009; 83(3):1240-1259.
Deamer et al., Large Volume Liposomes by an Ether Vaporization Method, Biochimica et Biophysica Acta, 1976; 443:629-634.

(56) References Cited

OTHER PUBLICATIONS

Diaz et al., Synthesis of Disulfide-Containing Phospholipid Analogs for the Preparation of Head Group-Specific Lipid Antigens: Generation of Phosphatidylserine Antibodies, Bioconjugate Chemistry, 1998; 9(2):250-254.

Dijkstra et al., Modulation of the Biological Activity of Bacterial Endotoxin by Incorporation Into Liposomes, Journal of Immunology, 1987; 138(8):2663-2670.

Dijkstra et al., Interaction of Anti-Cholesterol Antibodies with Human Lipoproteins, Journal of Immunology, 1996; 157(5):2006-2013.

Feijoo et al., Effects of Microfluidizer Technology on *Bacillus licheniformis* Spores in Ice Cream Mix, Journal of Dairy Science, 1997; 80(9):2184-2187.

Fernandes et al., Synthetic Lipopeptides Incorporated in Liposomes: In Vitro Stimulation of the Proliferation of Murine Splenocytes and In Viv0 Induction of an Immune Response Against a Peptide Antigen, Molecular Immunology, 1997; 34(8-9):569-576.

Fleiner et al., Studies on Protein-Liposome Coupling Using Novel Thiol-Reactive Coupling Lipids: Influence of Spacer Length and Polarity, Bioconjugate Chem., 2001; 12 (4), 470-475.

Frey et al., A fusion-intermediate state of HIV-1 gp41 targeted by broadly neutralizing antibodies, Proceedings of the National Academy of Sciences, 2008; 105(10):3739-3744.

Friede et al., Selective induction of protection against influenza virus infection in mice by a lipid-peptide conjugate delivered in liposomes, Vaccine, 1994; 12(9):791-797.

Frisch et al., Parameters affecting the immunogenicity of a liposome-associated synthetic hexapeptide antigen, European Journal of Immunology, 1991; 21(1):185-193.

Fujii et al., The VesiVax system: a method for rapid vaccine development, Frontiers in Bioscience, 2008; 13:1968-1980.

Garrity et al., Refocusing Neutralizing Antibody Response by Targeted Dampening of an Immunodominant Epitope, , Journal of Immunology, 1997; 159(1):279-289.

Giannecchini et al., Antibodies Generated in Cats by a Lipopeptide Reproducing the Membrane-Proximal External Region of the Feline Immunodeficiency Virus Transmembrane Enhance Virus Infectivity, Clinical and Vaccine Immunology, 2007; 14(8):944-951.

Haynes et al., HIV-1 Hides an Achilles' Heel in Virion Lipids, Immunity, 2008; 28(1):10-12.

Kamala T. , Hock immunization: A humane alternative to mouse footpad injections, Journal of Immunological Methods, 2007; 328(1-2): 204-214.

Hosmalin et al., Lipopeptide presentation pathway in dendritic cells, Immunology Letters, 2001; 79(1-2):97-100.

Huang et al., Partition Coefficients of Fluorescent Probes With Phospholipid Membranes, Biochemical and Biophysical Research Communications, 1991; 181(1):166-171.

Huarte et al., Lipid modulation of membrane-bound epitope recognition and blocking by HIV-1 neutralizing antibodies, FEBS Letters, 2008; 582(27):3798-3804.

Jeffery et al., The Preparation and Characterization of Poly(lactide-co-glycolide) Microparticles. II. The Entrapment of a Model Protein Using a (Water-in-Oil)-in-Water Emulsion Solvent Evaporation Technique, Pharmaceutical Research, 1993; 10(3):362-368.

Karasavvas et al., Antibodies induced by liposomal protein exhibit dual binding to protein and lipid epitopes, Biochemical and Biophysical Research Communications, 2008; 366(4):982-987.

Karlsson Hedestam et al., The challenges of eliciting neutralizing antibodies to HIV-1 and to influenza virus, Nature Reviews Microbiology, 2008; 6(2):143-155.

Law et al., Antigenic and Immunogenic Study of Membrane-Proximal External Region-Grafted gp120 Antigens by a DNA Prime-Protein Boost Immunization Strategy, Journal of Virology, 2007; 81(8):4272-4285.

Lenz et al., Trimeric Membrane-anchored gp41 Inhibits HIV Membrane Fusion, Journal of Biological Chemistry, 2005; 280(6):4095-4101.

Liang et al., Epitope insertion into variable loops of HIV-1 gp120 as a potential means to improve immunogenicity of viral envelope protein, Vaccine, 1999; 17(22):2862-2872.
Liao et al., Lipid Rafts and HIV Pathogenesis: Virion-Associated Cholesterol Is Required for Fusion and Infection of Susceptible Cells, AIDS Research and Human Retroviruses, 2003; 19(8):675-687.
Li et al., Peptide Environment Specifies Conformation, Journal of Biological Chemistry, 1993; 268(31):22975-22978.
Locksley et al., Helper T-cell subsets in mouse leishmaniasis: induction, expansion and effector function, Immunology Today, 1991; 12(3):A58-A61.
Luo et al., Induction of neutralizing antibody against human immunodeficiency virus type 1 (HIV-1) by immunization with gp41 membrane-proximal external region (MPER) fused with porcine endogenous retrovirus (PERV) p15E fragment, Vaccine, 2006; 24(4):435-42.
The Extended European Search Report and Written Opinion issued in EP 10751306 dated Jul. 12, 2013.
Chang et al., Immunogenicity of synthetic HIV-1 V3 loop peptides by MPL adjuvanted pH-sensitive liposomes. Vaccine Mar. 17, 1999;17(11-12):1540-1548.
Grundner et al., Solid-Phase Proteoliposomes Containing Human Immunodeficiency Virus Envelope Glycoproteins. J Virol. Apr. 2002;76(7):3511-3521.
Kinsky et al., An Alternative Procedure for the Preparation of Immunogenic Liposomal Model Membranes. J Immunol Methods Dec. 30, 1983;65(3);295-306.
Maeda and Fujimoto, A reduction-triggered delivery by a liposomal carrier possessing membrane-permeable ligands and a detachable coating. Colloids Surf B Biointerfaces, Apr. 15, 2006;49(1):15-21.
Pauillac et al., Application of a modified version of Habeeb's trinitrophenylation method for the characterization of hapten-protein conjugates in a reversed micellar medium. J Immunol Methods May 1, 2002;263(1-2):75-83.

* cited by examiner

METHODS AND COMPOSITIONS FOR LIPOSOMAL FORMULATION OF ANTIGENS AND USES THEREOF

RELATED APPLICATIONS

The present application claims priority from U.S. Provisional Patent Application 61/158,694 entitled "Methods and Compositions for Liposomal Formulation of Antigens and Uses Thereof," which was filed Mar. 9, 2009, and which is hereby incorporated in its entirety including all tables, figures, and claims.

STATEMENT AS TO FEDERALLY SPONSORED RESEARCH

The U.S. Government has a paid-up license in this invention and the right in limited circumstances to require the patent owner to license others on reasonable terms as provided for by the terms of National Institute of Allergy and Infectious Diseases (NIH) Grant No. 1R43AI077119-01; Grant No. NIH R01 GM061851; National Institutes of Health, University of California, San Francisco—Gladstone Institute of Virology & Immunology Center for AIDS Research, P30-AI027763; and U.S. Department of Homeland Security Graduate Fellowship contract number DE-AC05-00OR22750.

BACKGROUND OF THE INVENTION

The following discussion of the background of the invention is merely provided to aid the reader in understanding the invention and is not admitted to describe or constitute prior art to the present invention.

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their non-toxic nature, biodegradability, biocompatibility, adjuvanticity, induction of cellular immunity, property of sustained release and prompt uptake by macrophages, makes them attractive candidates for the delivery of antigens.

Liposomes have been demonstrated to induce both humoral and cell-mediated immunity to a large variety of bacterial, protozoan, viral and tumour cell antigens. While the widespread use of liposomal vaccines has been long anticipated, few such vaccines have been developed commercially. The immunoadjuvant action of liposomes depends on various structural characteristics. Such characteristics include the three-dimensional conformation of the antigen being presented by the liposome, which may not always mimic the natural conformation of the antigen.

For example, the membrane proximal region (MPR) of HIV gp41, a segment comprised of approximately 35 amino acids N terminal to the transmembrane domain, has been considered a desirable vaccine target because it is well conserved across viral clades and is essential for virus-cell fusion. However, efforts to date have not succeeded in eliciting a useful immune response, and attempts to present structurally constrained epitopes, either conjugated to carrier proteins or grafted on recombinant constructs, have not elicited neutralizing antibodies. In addition to a lack of consensus regarding the epitope structure, the relatively weak immunogenicity of the MPR may result in immune responses to recombinant envelope immunogens directed toward immunodominant regions on gp41 that mask the MPR from antibody recognition.

In addition, such characteristics may also include factors which control vesicle fate in vivo. Methods for associating an antigen with a liposome prior to liposome formation often expose the antigen to detergents and/or organic solvents. In contrast, methods for associating an antigen with a liposome following formation can expose the liposome to unfavorable chemical treatments. Liposomes may be quickly cleared by the reticuloendothelial system and macrophages, reducing the efficiency of the liposome as a vaccine.

There remains in the art a need for methods and compositions which can provide liposomal vaccines that deliver antigens in a manner useful for stimulating an immune response.

BRIEF SUMMARY OF THE INVENTION

It is an object of the invention to provide liposomal vaccine compositions, methods for the manufacture thereof, and methods for the use thereof to stimulate an immune response in an animal.

In one aspect, the invention relates to a composition comprising one or more immunogenic polypeptides or carbohydrates of interest. The compositions of the present invention comprise:
 a) an aqueous vehicle;
 b) liposomes comprising
  (i) dimyristoylphosphatidylcholine ("DMPC"),
  (ii) dimyristoylphosphatidylglycerol ("DMPG"), dimyristoyltrimethylammonium propane ("DMTAP"), or both DMPG and DMTAP, and
  (iii) at least one sterol derivative; and
 c) one or more immunogenic polypeptide(s) or carbohydrate(s) covalently linked to between 1% and 100% of said at least one sterol derivative.

And in a related aspect, the invention relates to a composition comprising one or more immunogenic polypeptides or carbohydrates of interest. The compositions of the present invention comprise:
 a) an aqueous vehicle; and
 b) liposomes comprising
  (i) dimyristoylphosphatidylcholine ("DMPC"),
  (ii) dimyristoylphosphatidylglycerol ("DMPG"), dimyristoyltrimethylammonium propane ("DMTAP"), or both DMPG and DMTAP, and
  (iii) at least one reactive sterol derivative,
  wherein between 1% and 100% of said at least one sterol derivatives comprise a functional moiety covalently attached thereto, said functional moiety selected from the group consisting of an amine reactive group, a sulfhydryl reactive group, a carboxyl reactive group, a photoaffinity reactive group, an arginine linking group, and a carbonyl reactive group.

For the sake of convenience, the lipid(s) selected in part (ii) above will be referred to below as DMPG/DMTAP, which is intended to mean DMPG, DMTAP, or a mixture of the two. In certain embodiments, the relative percentages of DMPC, DMPG/DMTAP, and sterol derivative are 50% to 98% DMPC: 1% to 25% DMPG/DMTAP: 1% to 25% sterol derivative, and in certain other embodiments 70% to 98% DMPC: 1% to 15% DMPG/DMTAP: 1% to 15% sterol derivative. This is not meant to imply that no other components are present in the liposome; rather, these represent the relative percentages of DMPC, DMPG/DMTAP, and sterol derivative on a molar basis to one another. In certain embodiments, a liposome can also contain one or more additional components which are well known in the art, such as peptidoglycan, lipopeptide, lipopolysaccharide, monophosphoryl lipid A, lipoteichoic acid, resiquimod, imiquimod, flagellin, oligonucleotides containing unmethylated CpG motifs, α-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyltrimethylammoniumpropane, and nod-like receptor agonists.

In preferred embodiments, these relative percentages are 70% to 85% DMPC: 5% to 15% DMPG/DMTAP: 10% to 15% sterol derivative, and more preferably about 75% DMPC, about 10% DMPG/DMTAP, and about 15% sterol derivative. The term "about" as used herein in this context refers to +/−10% of a given measurement. DMPG is particularly preferred as the lipid selected in part (ii) above.

The term "sterol derivative" as used herein refers to any molecule having the 4-member ring structure characteristic of steroids and a hydroxyl (—OH) or ester (—OR) substitution at the 3-carbon position, and some or all of which serves as an anchor for attaching an immunogenic polypeptide or carbohydrate to a liposome:

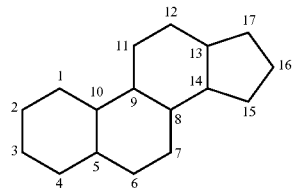 [SMILES: C1CCC2C(C1)CCC1C3CCCC3CCC21]

The skilled artisan will understand that a sterol derivative can be further substituted at one or more of the other ring carbons, and may also contain various double bonds in the rings. In certain embodiments, a sterol derivative is a derivative in which the immunogenic polypeptide or carbohydrate is covalently linked to the steroid ring structure via the 3-carbon position, or via the 17 carbon position. Preferred sterol derivatives include derivatives of cholesterol, cholesteryl chloroformate, stigmasterol, sitosterol, ergosterol, lanosterol, desmosterol, and campesterol. This list is not meant to be limiting.

In preferred embodiments, these sterol derivatives are cholesterol derivatives. A cholesterol derivative is substituted at the 8-, 10-, and 13-carbon positions with methyl groups and contains a double bond at the 5,6-carbon position. Most preferably, the sterol derivatives have the following structure:

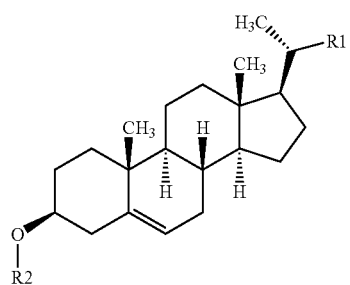

wherein:
one of R1 or R2 is a covalent linkage to an immunogenic polypeptide or carbohydrate, wherein if R1 is said covalent linkage to said polypeptide, R2 is H, and if R2 is said covalent linkage to said immunogenic polypeptide, R1 is —CH$_2$—CH$_2$—CH$_2$—C(H)(CH$_3$)$_2$.

In particularly preferred embodiments, R1 is —CH$_2$—CH$_2$—C(O)—X, wherein X is an immunogenic polypeptide or carbohydrate, and R2 is H. In other particularly preferred embodiments, R1 is —CH$_2$—CH$_2$—CH$_2$—C(H)(CH$_3$)$_2$, and R2 is —C(O)—CH$_2$—CH$_2$—C(O)—X, wherein X is an immunogenic polypeptide or carbohydrate.

In other preferred embodiments, these sterol derivatives are cholesterol derivatives. A cholesterol derivative is substituted at the 8-, 10-, and 13-carbon positions with methyl groups and contains a double bond at the 5,6-carbon position. Most preferably, the sterol derivatives have the following structure:

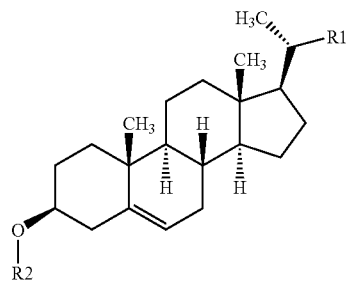

wherein:
one of R1 or R2 is comprise a functional moiety covalently attached thereto, wherein said functional moiety is selected from the group consisting of an amine linking group, a sulfhydryl linking group, a carboxyl linking group, a photoaffinity linking group, an arginine linking group, and a carbonyl linking group, and wherein
if R1 is said functional moiety, R2 is H, and
if R2 is said functional moiety, R1 is —CH$_2$—CH$_2$—CH$_2$—C(H)(CH$_3$)$_2$.

In certain embodiments, the liposome are provided within a particular average size range, as size can affect the efficiency with which liposomes are taken up when delivered mucosally, and/or cleared when delivered intravenously. Liposome size can be determined by methods well known in the art, including photon correlation spectroscopy, dynamic light scattering, etc. In preferred embodiments, the liposomes are substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

As noted above, some or all of a steroid derivative which is a component part of the liposome serves as an anchor for attaching an immunogenic polypeptide or carbohydrate to a liposome. In preferred embodiments, said one or more immunogenic polypeptide(s) are covalently linked to between about 1% and about 25% of the sterol derivative(s), and most preferably between about 5% and 10% of the sterol derivative(s). The term "about as used herein in this context refers to +/−20% of a recited percentage.

As is also noted above, the liposomes of the present invention may also comprise one or more additional components, such as peptidoglycan, lipopeptide, lipopolysaccharide, monophosphoryl lipid A, lipoteichoic acid, resiquimod, imiquimod, flagellin, oligonucleotides containing unmethylated CpG motifs, a-galactosylceramide, muramyl dipeptide, all-trans retinoic acid, double-stranded viral RNA, heat shock proteins, dioctadecyldimethylammonium bromide, dimyristoyltrimethylammoniumpropane, cationic surfactants, toll-like receptor agonists, and nod-like receptor agonists. These additional components can serve as additional adjuvant materials. In certain embodiments, the relative percentage of such an additional component is less than 10% of the total of DMPC, DMPG/DMTAP, and sterol derivative on a molar basis. More preferably, the relative percentage of such an additional component is less than 2% of the total of DMPC, DMPG/DMTAP, and sterol derivative on a molar basis, and most preferably less than 1% of the total of DMPC, DMPG/DMTAP, and sterol derivative on a molar basis.

Methods for covalently linking an immunogenic polypeptide or carbohydrate to a sterol derivative are well known in the art. Chemical cross-linkers are discussed in numerous books and catalogues. See, e.g., Wong, *Chemistry of Protein Conjugation and Cross-linking*, CRC Press, Boca Raton, Fla., 1991. These reagents often employ functional groups that couple to amino acid side chains of peptides. Moieties that can be targeted using a cross-linker include primary and ε-amines, sulfhydryls, carbonyls, hydroxyls, and carboxylic acids. In addition, many reactive groups can be coupled non-selectively using a cross-linker such as photoreactive phenyl azides.

In the case of immunogenic polypeptide(s), these may be preferably covalently linked to one or more sterol derivatives through one or more of the following: a lysine residue on the immunogenic polypeptide(s), through a cysteine residue on the immunogenic polypeptide(s), through an aspartate residue on the immunogenic polypeptide(s), through a glutamate residue on the immunogenic polypeptide(s), through a serine residue on the immunogenic polypeptide(s), through a threonine residue on the immunogenic polypeptide(s), through an N-terminal amine on the immunogenic polypeptide(s), and/or through a C-terminal carboxyl on the immunogenic polypeptide(s). In the case of immunogenic carbohydrates, these may be preferably covalently linked through a hydroxyl on the immunogenic carbohydrate.

A covalent linkage between an immunogenic polypeptide or carbohydrate and a sterol derivative may be as short as a covalent bond between a sterol ring atom or sterol side chain atom, but preferably provides one or more linker atoms connecting the immunogenic polypeptide or carbohydrate to the sterol derivative. Preferred linkages are $C_{1-18}$ alkylene straight or branched chain comprising from 0-4 backbone (i.e., non-substituent) heteroatoms, optionally substituted with from 1 to 4 substituents independently selected from the group consisting of $C_{1-6}$ alkyl straight or branched chain, halogen, $C_{1-6}$ alkoxy, $-NO_2$, $-NH_2$, $=O$, $-OH$, $-CH_2OH$, trihalomethyl, $-C(O)NH_2$ and $-C(O)(OR4)$ where R4 is H or $C_{1-3}$ alkyl.

The inclusion of polymer portions (e.g., polyethylene glycol ("PEG") homopolymers, polypropylene glycol homopolymers, other polyalkylene oxides, bis-polyethylene oxides and co-polymers or block co-polymers of poly(alkylene oxides)) in cross-linkers can, under certain circumstances be advantageous. See, e.g., U.S. Pat. Nos. 5,643,575, 5,672,662, 5,705,153, 5,730,990, 5,902,588, and 5,932,462; Fleiner et al., *Bioconjug. Chem.* 12 (4), 470-75, 2001; and Topchieva et al., *Bioconjug. Chem.* 6: 380-8, 1995). A preferred linkage to between an immunogenic polypeptide or carbohydrate and a sterol derivative comprises an (alkylene oxide)$_n$ moiety having an average length n of between 40 and 1000. Suitable polyalkylene oxides include, but are not limited to, homopolymers and copolymers comprising methylene oxide, ethylene oxide, propylene oxide, isopropylene oxide, and butylene oxide.

In particularly preferred embodiments, a covalent linkage between an immunogenic polypeptide or carbohydrate and a sterol derivative has the structure St-R3-X, wherein:

St is a ring atom of the sterol derivative;

R3 is $C_{0-18}$ straight or branched chain alkyl, or $C_{0-12}$ straight or branched chain alkyl-(alkylene oxide)$_n$-$C_{0-12}$ straight or branched chain alkyl, wherein n is on average between 40 and 1000; each said straight or branched chain alkyl comprises from 0-4 chain heteroatoms and one or more substituents independently selected from the group consisting of halogen, trihalomethyl, $-C_{1-6}$ alkoxy, $-NO_2$, $-NH_2$, $-OH$, $-CH_2OH$, $-CONH_2$, and $-C(O)(OR4)$ where R4 is H or $C_{1-3}$ alkyl; and X is an atom of the immunogenic polypeptide or carbohydrate.

In preparing the immunogenic polypeptide-linked sterol derivatives, it is advantageous to prepare an intermediate sterol derivative in which the linkage chemistry terminates in a reactive group which forms a covalent bond with a reactive partner on the immunogenic polypeptide of interest. As discussed above, suitable reactive partners include free amines, sulfhydryls, carboxyls, arginines, carbonyls, etc. Thus, in another aspect, the present invention also relates to reactive sterol derivatives.

In preferred embodiments, these reactive sterol derivatives are cholesterol derivatives. A cholesterol derivative is substituted at the 8-, 10-, and 13-carbon positions with methyl groups and contains a double bond at the 5,6-carbon position. Most preferably, the sterol derivatives have the following structure:

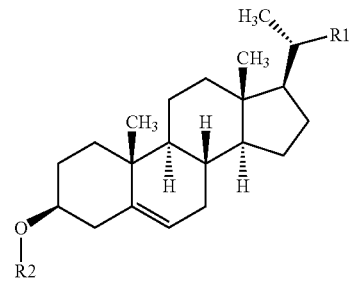

wherein:

one of R1 or R2 is a covalent linkage comprising a reactive group which reacts to form a covalent bond with a reactive partner on an immunogenic polypeptide of interest, wherein if R1 is said covalent linkage to said polypeptide, R2 is H, and if R2 is said covalent linkage to said immunogenic polypeptide, R1 is $-CH_2-CH_2-CH_2-C(H)(CH_3)_2$.

In particularly preferred embodiments, R1 is $-CH_2-CH_2-C(O)-RG$, wherein RG is a reactive group, and R2 is H. In other particularly preferred embodiments, R1 is $-CH_2-CH_2-CH_2-C(H)(CH_3)_2$, and R2 is $-C(O)-CH_2-CH_2-C(O)-RG$, wherein RG is a reactive group. Preferred reactive groups are selected from the group consisting of imidoesters, N-hydroxysuccinimidyl ("NHS") esters, maleimides, alkyl halides, aryl halides, α-haloacyls, pyridyl disulfides, carbodiimides, glyoxals, amines, hydrazides, and arylazides. See, e.g., Wong, *Chemistry of Protein Conjugation and Cross-linking*, CRC Press, Boca Raton, Fla., 1991.

A covalent linkage between a sterol derivative and a reactive group may be as short as a covalent bond between a sterol ring atom or sterol side chain atom, but preferably provides one or more linker atoms connecting the sterol ring atom or sterol side chain atom to the reactive group. Preferred linkages are $C_{1-18}$ alkylene straight or branched chain comprising from 0-4 backbone (i.e., non-substituent) heteroatoms, optionally substituted with from 1 to 4 substituents independently selected from the group consisting of $C_{1-6}$ alkyl straight or branched chain, halogen, $C_{1-6}$ alkoxy, —$NO_2$, —$NH_2$, =O, —OH, —$CH_2OH$, trihalomethyl, —$C(O)NH_2$ and —$C(O)(OR4)$ where R4 is H or $C_{1-3}$ alkyl.

In other preferred embodiments, a covalent linkage between a sterol derivative and a reactive group has the structure St-R3-RG, wherein:

St is a ring atom of the sterol derivative;

R3 is $C_{0-18}$ straight or branched chain alkyl, or $C_{0-12}$ straight or branched chain alkyl-(alkylene oxide)$_n$-$C_{0-12}$ straight or branched chain alkyl, wherein n is on average between 40 and 1000; each said straight or branched chain alkyl comprises from 0-4 chain heteroatoms and one or more substituents independently selected from the group consisting of halogen, trihalomethyl, —$C_{1-6}$ alkoxy, —$NO_2$, —$NH_2$, —OH, —$CH_2OH$, —$CONH_2$, and —$C(O)(OR4)$ where R4 is H or $C_{1-3}$ alkyl; and RG is a reactive group.

In another aspect, the invention relates to methods for preparing compositions comprising one or more immunogenic polypeptides or carbohydrates of interest. These methods comprise:

(a) covalently coupling one or more immunogenic polypeptides or carbohydrates to one or more sterol derivatives to provide one or more conjugated sterol derivatives; and (b) combining
  (i) dimyristoylphosphatidylcholine ("DMPC"),
  (ii) dimyristoylphosphatidylglycerol ("DMPG"), dimyristoyltrimethylammonium propane ("DMTAP"), or both DMPG and DMTAP, and
  (iii) one or more sterol derivatives, wherein between 1% and 100% of said sterol derivative(s) is(are) said conjugated sterol derivative(s) to provide a lipid mixture; and (c) preparing liposomes from said lipid mixture.

In a related aspect, the invention relates to methods for preparing the foregoing compositions comprising one or more immunogenic polypeptides or carbohydrates of interest. These methods comprise:

(a) combining
  (i) dimyristoylphosphatidylcholine ("DMPC"),
  (ii) dimyristoylphosphatidylglycerol ("DMPG"), dimyristoyltrimethylammonium propane ("DMTAP"), or both DMPG and DMTAP, and
  (iii) at least one sterol derivative to provide a lipid mixture;

(b) preparing liposomes from said lipid mixture; and (c) covalently coupling one or more immunogenic polypeptides or carbohydrates to said at least one sterol derivative, wherein said one or more immunogenic polypeptide(s) or carbohydrate(s) are covalently linked to between 1% and 100% of said at least one sterol derivative.

Suitable methods for preparing liposomes from lipid mixtures are well known in the art. See, e.g., Basu & Basu, *Liposome Methods and Protocols* (*Methods in Molecular Biology*), Humana Press, 2002; Gregoriadis, *Liposome Technology, 3rd Edition*, Informa HealthCare, 2006. Preferred methods include extrusion, homogenization, and sonication methods described therein. An exemplary method for preparing liposomes of the invention, which comprises drying a lipid mixture, followed by hydration in an aqueous vehicle and sonication to form liposomes, is described hereinafter. Preferred steroid derivatives, methods for covalently coupling immunogenic polypeptides or carbohydrates to such derivatives, and covalent linkages are discussed in detail above and hereinafter.

In certain embodiments, the relative percentages of DMPC, DMPG/DMTAP, and sterol derivative are 50% to 98% DMPC: 1% to 25% DMPG/DMTAP: 1% to 25% sterol derivative, and in certain other embodiments 70% to 98% DMPC: 1% to 15% DMPG/DMTAP: 1% to 15% sterol derivative. As discussed above, this is not meant to imply that no other components are present in the lipid mixture (and hence in the liposomes); rather, these represent the relative percentages of DMPC, DMPG/DMTAP, and sterol derivative on a molar basis to one another. In certain embodiments, a lipid mixture can also contain one or more additional components which are well known in the art, such as peptidoglycan, lipopeptide, lipopolysaccharide, monophosphoryl lipid A, lipoteichoic acid, resiquimod, imiquimod, flagellin, oligonucleotides containing unmethylated CpG motifs, a-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyltrimethylammonium-propane, and nod-like receptor agonists.

In preferred embodiments, these relative percentages are 70% to 85% DMPC: 5% to 15% DMPG/DMTAP: 10% to 15% sterol derivative, and more preferably about 75% DMPC, about 10% DMPG/DMTAP, and about 15% sterol derivative. The term "about" as used herein in this context refers to +/−10% of a given measurement. DMPG is particularly preferred as the lipid selected in part (ii) above.

In certain embodiments, methods further comprise selecting liposomes within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

In another aspect, the invention relates to methods for immunizing an animal, preferably a mammal and most preferably a human, with one or more immunogenic polypeptides or carbohydrates of interest. These methods comprise:

delivering to said animal by a parenteral or enteral route an effective amount of a liposomal composition comprising:
a) an aqueous vehicle;
b) liposomes comprising
  (i) dimyristoylphosphatidylcholine ("DMPC"),
  (ii) dimyristoylphosphatidylglycerol ("DMPG"), dimyristoyltrimethylammonium propane ("DMTAP"), or both DMPG and DMTAP, and
  (iii) at least one sterol derivative; and
c) one or more immunogenic polypeptide(s) or carbohydrate(s) covalently linked to between 1% and 100% of said at least one sterol derivative.

Preferred liposomal compositions, methods for making such compositions, steroid derivatives, methods for covalently coupling immunogenic polypeptides or carbohydrates to such derivatives, and covalent linkages are discussed in detail above and hereinafter.

Preferred enteral routes of administration include delivery by mouth (oral), nasal, rectal, and vaginal routes. Preferred parenteral routes of administration include intravenous, intramuscular, subcutaneous, and intraperitoneal routes.

In certain embodiments, the methods of the present invention comprise multiple deliveries of an immunogenic polypeptide or carbohydrate, commonly referred to as "prime/boost" immunization protocol. In preferred embodiments, one or more of the prime and boost deliveries comprises delivering to the animal by a parenteral or enteral route a liposomal composition of the present invention. In such immunization protocols, a priming delivery may be via a different route of administration than one or more boost deliveries. For example, a priming delivery may be made by subcutaneous delivery of an immunogen, and a boost delivery may be made by intramuscular delivery.

In addition, the prime and one or more boost deliveries of an antigen of interest may be "homologous," meaning that both the prime and boost comprises delivery of a liposomal composition of the invention; or may be "heterologous," meaning that one of the prime or boost deliveries comprises delivery of a liposomal composition of the present invention, while another delivery may be made by means of a different vaccine platform. Such alternative vaccine platforms include, but are not limited to, delivery of antigen in a non-liposomal vaccine formulation, delivery of DNA vaccine encoding the antigen, delivery of a recombinant viral vaccine, etc.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Figure 1:
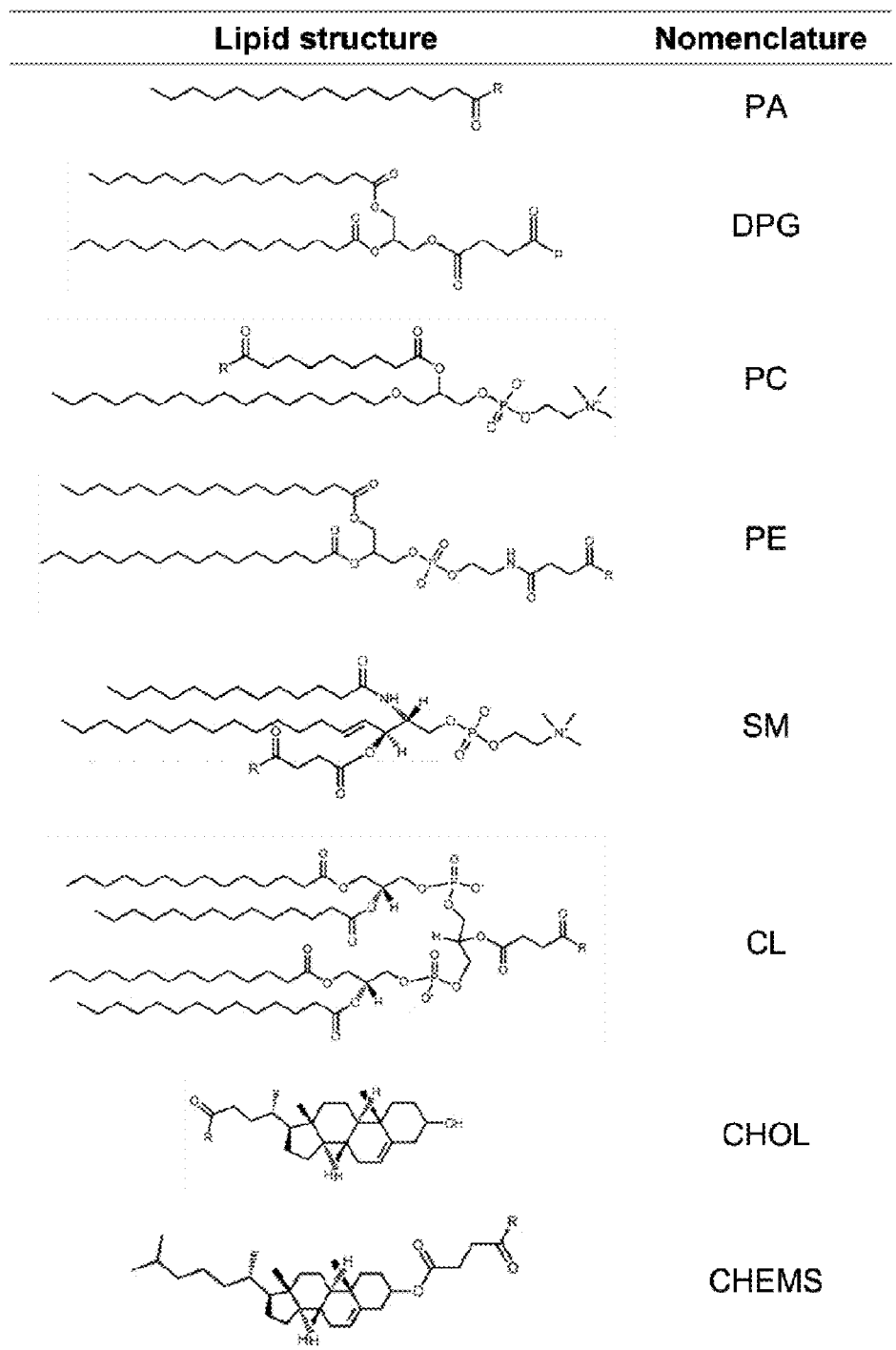
FIG. 1 depicts lipid structures used in exemplary embodiments. R indicates the location of attachment of antigens to the lipids.

Coupling through Sulfhydryl Groups:

Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

Coupling Through Carboxyl Groups:

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

Nonselective Reactive Groups:

A photoaffinity reagent is a compound that is chemically inert but becomes reactive when exposed to ultraviolet or visible light. Arylazides are photoaffinity reagents that are photolyzed at wavelengths between 250-460 nm, forming a reactive aryl nitrene. The aryl nitrene reacts nonselectively to form a covalent bond. Reducing agents must be used with caution because they can reduce the azido group.

Coupling Through Arginines:

Glyoxals are useful compounds for targeting the guanidinyl portion of arginine residues. Glyoxals will target arginines at mildly alkaline pH. There is some cross-reactivity (the greatest at higher pH) with lysines.

Coupling Through Carbonyl Groups:

Carbonyls (aldehydes and ketones) react with amines and hydrazides at pH 5-7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones. For carbohydrates with reducing end(s), the carbonyl group(s) can be reactive towards a hydrazine moiety to form a hydrazone bond. S-HyNic is a heterobifunctional linker used to incorporate HyNic (6-hydrazinonicotinamide) moieties into molecules through a free amino group via an activated ester (i.e. NHS). The addition of a HyNic hydrazine linker permits formation of a conjugate in slightly acidic buffer (100 mM $NaPO_4$, pH6). For carbohydrates without a reducing end, CDAP specific activation may be used. Under mild conditions (pH 9.5 for activation and pH 7 for conjugation), 1-cyano-4-dimethylaminopyridinium tetrafluoroborate ("CDAP") converts hydroxyl groups to cyanyl esters which will then form carbamates in the presence of amine groups.

A functional moiety can be attached directly to a ring atom on the polycyclic sterol nucleus, or may be attached to the sterol nucleus through one or more linking atoms. An exemplary covalent linkage between a sterol and a reactive group has the structure St-R3-X, wherein:

St is a ring atom of the sterol derivative;

R3 is $C_{0-18}$ straight or branched chain alkyl, or $C_{0-12}$ straight or branched chain alkyl-(alkylene oxide)$_n C_{0-12}$ straight or branched chain alkyl, wherein n is on average between 40 and 1000, wherein each said straight or branched chain alkyl comprises from 0-4 chain heteroatoms and one or more substituents independently selected from the group consisting of halogen, trihalomethyl, $-C_{1-6}$ alkoxy, $-NO_2$, $-NH_2$, $-OH$, $-CH_2OH$, $-CONH_2$, and $-C(O)(OR4)$ where R4 is H or $C_{1-3}$ alkyl; and X is a reactive linking group, most preferably an amine linking group, a sulfhydryl linking group, a carboxyl linking group, a photoaffinity linking group, an arginine linking group, and a carbonyl linking group.

The polymeric substances optionally included in the linkage chemistry are preferably poly(alkylene oxides). As used herein, the term "alkylene oxide" refers to the structure, $-X-O-$, where X is an alkylene moiety covalently linked to oxygen 0; thus poly(alkylene oxide) refers to the structure $-(X-O-)_m-$. It is preferred that the poly(alkylene oxide) polymer be a nonbranched homopolymer (i.e., a polymer of the structure $-((CH_2)_n-O-)_m-$ in which n does not vary) such as poly(ethylene oxide) derived from ethylene glycol. Alternative polymers such as other polyalkylene oxide homopolymers (e.g., methylene oxide, propylene oxide, isopropylene oxide, and butylene oxide polymers) and co-polymers or block co-polymers of poly(alkylene oxides) may also be used. In those aspects of the invention where PEG-based polymers are used, it is preferred that they have average length n of between 40 and 1000 monomeric units. Molar equivalent amounts of the other alkylene oxides may be determined readily by those of ordinary skill in the art to arrive at preferred average molecular weights for other homopolymers and copolymers.

Average molecular weights of the present invention are measured using the "number-average" method. In a mixture of polymer molecules with different molecular weights in which the number of molecules having a particular molecular weight, $M_i$, is given by $N_i$, the "number-average" probability of a given mass being present is $$P_i = \frac{N_i}{\sum_{j=0}^{\infty} N_j}$$

and the number-average molecular weight is given by the formula $$\overline{M_n} = \sum_{i=0}^{\infty} \left( \frac{N_i}{\sum_{j=0}^{\infty} N_j} \right) M_i = \frac{\sum_{i=0}^{\infty} N_i M_i}{\sum_{j=0}^{\infty} N_j}$$

The number average is the simple arithmetic mean, representing the total weight of the molecules present divided by the total number of molecules. The number-average molecular weight of a polymer may be measured by vapor pressure osmometry using methods and apparatuses well known to those of skill in the art.

Alternative polymeric substances which may be used in place of poly(alkylene oxides) include materials such as dextran, polyvinyl pyrrolidones, polysaccharides, starches, polyvinyl alcohols, polyacryl amides or other similar polymers. Those of ordinary skill in the art will realize that the foregoing is merely illustrative and not intended to restrict the type of non-antigenic polymeric substances suitable for use herein.

"Administration" as used herein with respect to an animal, including preferably a mammal and most preferably a human, refers to delivery of an exogenous reagent to a cell, tissue, organ, or biological fluid of the subject.

"Effective amount" as used herein refers to an amount of a reagent that can ameliorate, reverse, mitigate, or prevent a symptom or sign of a medical condition or disorder. Unless dictated otherwise, explicitly or otherwise, an "effective amount" is not limited to a minimal amount sufficient to ameliorate a condition, or to an amount that results in an optimal or a maximal amelioration of the condition. "Effective amount" within the context of administration of a vaccine is that which causes an immune response in the mammal. Such an effective amount may not be, in and of itself, sufficient to cause such an immune response, but may be used together with previous or subsequent delivery of additional reagents (e.g. a prime-boost vaccination). An "immunological response" or "immune response" as used herein encompasses at least one or more of the following effects: the production of antibodies by B-cells; and/or the activation of suppressor T-cells and/or T-cells directed specifically to an antigen or antigens present in the vectors, composition or vaccine of interest.

A variety of in vitro and in vivo assays are known in the art for measuring an immune response, including measuring humoral and cellular immune responses, which include but are not limited to standard immunoassays, such as RIA, ELISA assays; intracellular staining; T cell assays including for example, lymphoproliferation (lymphocyte activation) assays, CTL cytotoxic cell assays, or by assaying for T-lymphocytes specific for the antigen in a sensitized subject. Such assays are well known in the art.

The preparation of liposomes is well known in the prior art. In general, liposomes have been made by a number of different techniques including ethanol injection (Batzri et al., *Biochem. Biophys. Acta.* 298:1015, 1973); ether infusion (Deamer et al., *Biochem. Biophys. Acta.* 443:629, 1976; Schieren et al., *Biochem. Biophys. Acta.* 542:137, 1978); detergent removal (Razin, *Biochem. Biophys. Acta.* 265:24 1972); solvent evaporation (Matsumato et al., *J. Colloid Interface Sci.* 62:149, 1977); evaporation of organic solvents from chloroform in water emulsions (REV's) (Szoka Jr. et al., *Proc. Natl. Acad. Sci. USA,* 75:4194, 1978); extrusions of MLVs or EUV's through a nucleopore polycarbonate membrane (Olson et al., *Biochem. Biophys. Acta.* 557:9, 1979); freezing and thawing of phospholipid mixtures (Pick, *Arch. Biochem. Biophys.,* 212:186, 1981), as well as sonication and homogenization. By convention, liposomes are categorized by size, and a 3-letter acronym is used to designate the type of liposome being discussed. Multilamellar vesicles are generally designated "MLV." Small unilamellar vesicles are designated "SUV," and large unilamellar vesicles are designated "LUV." These designations are sometimes followed by the chemical composition of the liposome. For a discussion of nomenclature and a summary of known types of liposomes, see Storm et al., *PSIT,* 1: 19-3, 1998.

The liposomal compositions of the invention may further comprise, either as part of the liposome itself or as part of the vehicle in which the liposomes are suspended, various excipients, adjuvants, carriers, auxiliary substances, modulating agents, and the like.

A carrier, which is optionally present, is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* 10:362, 1993; McGee et al., *J. Microencapsul.* 14: 197, 1997; O'Hagan et al., *Vaccine* 11:149, 1993. Such carriers are well known to those of ordinary skill in the art.

Adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L1 21, and MDP either microfluidized into a submicron emulsion or vortexed to generate a larger particle size emulsion, and (c) Ribi™ adjuvant system (RAS), (Ribi Immunochem, Hamilton, Mont.); (3) one or more bacterial cell wall components from the group consisting of monophosphorylipid A (MPL), trehalose dimycolate (TDM), and cell wall skeleton (CWS), preferably MPL+CWS (Detoxu); (4) saponin adjuvants, such as Stimulon™ (Cambridge Bioscience, Worcester, Mass.); (5) Complete Freunds Adjuvant (CFA) and Incomplete Freunds Adjuvant (IFA); (6) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (7) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (8) other substances that act as immunostimulating agents to enhance the effectiveness of the composition.

Preferred adjuvants include pathogen-associated molecular patterns (PAMPs), which mediate innate immune activation via Toll-like Receptors (TLRs), (NOD)-like receptors (NLRs), Retinoic acid inducible gene-based (RIG)-1-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, α-galactosylceramide, muramyl dipeptide. Peptidoglycans, lipoproteins, and lipoteichoic acids are cell wall components of Gram-positive.

Lipopolysaccharides are expressed by most bacteria, with MPL being one example. Flagellin refers to the structural component of bacterial flagella that is secreted by pathogenic and commensal bacterial. α-Galactosylceramide (α-GalCer) is an activator of natural killer T (NKT) cells. Muramyl dipeptide is a bioactive peptidoglycan motif common to all bacteria Other preferred adjuvants include viral double-stranded RNA, which is sensed by the intracellular receptor TLR3; CpG motifs present on bacterial or viral DNA or ssRNA, which are sensed by TLR7, 8, and 9; all-trans retinoic acid; and heat shock proteins such as HSP70 and Gp96, which are highly effective carrier molecules for cross-presentation. Pharmaceutical adjuvants include resiquimod, a TLR7/8 agonists, and imiquimod, a TLR7 agonist.

The liposomes of the present invention are preferably formulated as pharmaceutical compositions for parenteral or enteral delivery. A typical pharmaceutical composition for administration to an animal comprises a pharmaceutically acceptable vehicle such as aqueous solutions, non-toxic excipients, including salts, preservatives, buffers and the like. See, e.g., *Remington's Pharmaceutical Sciences,* 15th Ed., Easton ed., Mack Publishing Co., pp 1405-1412 and 1461-1487 (1975); *The National Formulary XIV, 14th Ed.,* American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to routine skills in the art.

Repeated administrations of a particular vaccine (homologous boosting) have proven effective for boosting humoral responses. Such an approach may not be effective at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting).

In a heterologous boosting regimen, at least one prime or boost delivery comprises delivery of the liposomal formulations described herein. The heterologous arm of the regimen may comprise delivery of antigen using one or more of the following strategies:

attenuated and/or inactivated bacteria or viruses comprising the antigen of interest, which are particles that have been treated with some denaturing condition to render them ineffective or inefficient in mounting a pathogenic invasion;

purified antigens, which are typically naturally-produced antigens purified from a cell culture of the pathogen or a tissue sample containing the pathogen, or a recombinant version thereof;

live viral or bacterial delivery vectors recombinantly engineered to express and/or secrete antigens in the host cells of the subject. These strategies rely on genetically engineering the viral vectors to be non-pathogenic and non-toxic;

antigen presenting cell (APC) vectors, such as a dendritic cell (DC) vector, which comprise cells that are loaded with an antigen, or transfected with a composition comprising a nucleic acid encoding the antigen;

tumor cells, for example, autologous and allogeneic tumor cells; and naked DNA vectors and naked RNA vectors which may be administered by a gene gun, electroporation, bacterial ghosts, microspheres, microparticles, liposomes, polycationic nanoparticles, and the like.

A prime vaccine and a boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, intratumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

EXAMPLE 1

Liposomes Conjugated to Hiv-1 gp41

Despite extensive research, attempts to elicit broadly neutralizing antibodies (bnAb) to HIV have not yet succeeded. The membrane proximal region (MPR) of HIV-1 gp41 is a desirable target for development of a vaccine that elicits neutralizing antibodies since the patient-derived monoclonal antibodies, 2F5 and 4E10, bind to MPR and neutralize primary HIV isolates. It has been demonstrated that two antibodies, designated 2F5 and 4E10, cross-react with lipids, and structural studies suggest that MPR immunogens may be presented in a membrane environment. However, efforts to date have not succeeded in eliciting antibodies with the breadth or potency of patient-derived antibodies.

The lipid reactivities of bnAb 2F5 and 4E10 have been a topic of intense study. Both antibodies have unusually long, hydrophobic CDRH3 regions and cross-react with phospholipids and other autoantigens. Moreover, biophysical models suggest that the MPR intercalates into the membrane in native virions. These observations have led to suggestions that MPR immunogens may be presented optimally in a lipid bilayer environment. The majority of strategies to insert the epitopes in a lipid environment have involved chimeric viruses or liposomal formulations of recombinant constructs with transmembrane peptide domains. Additionally, variations in lipid membrane composition appear to alter MPR peptide accessibility, and modulation of the peptide anchoring mechanism may exert similar effects.

We hypothesized that covalent attachment of lipid anchors would enhance the humoral immune response to MPR-derived peptides presented in liposomal bilayers. Three peptides were selected, corresponding to the 2F5 epitope (N-MPR), the 4E10 epitope (C-MPR) and a helically constrained peptide spanning both epitopes (NC-MPR). These epitopes are summarized in FIG. 1. We systematically examined the effects of the lipid anchors on the humoral response in mice immunized with the lipopeptides in liposomes.

A. Materials and methods

Amino acid building blocks, resins and coupling agents were obtained from Novabiochem (Darmstadt, Germany), Anaspec (San Jose, Calif.) or ChemPep (Miami, Fla.). Cholesterol, dimyristoylphosphatidylcholine (DMPC), dimyristoylphosphatidylglycerol (DMPG), oxidized phosphatidylcholine (PC; #870601), brain sphingomyelin (SM; #860082) and tetramyristoylcardiolipin (CL; #710332) were obtained from Avanti Polar Lipids (Alabaster, Ala.). Dipalmitoylphosphatidylethanolamine (PE; #LP-R4-019) and dipalmitoylglycerol (DPG; #LP-R4-028) were obtained from Genzyme Pharmaceuticals (Cambridge, Mass.). Palmitic acid (PA; #P5585) and 5-cholenic acid-3β-ol (CHOL; #C2650) were obtained from Sigma-Aldrich (St. Louis, Mo.). Anhydrous solvents of 99.8% or greater purity were obtained from Acros Organics (Geel, Belgium). Monophosphoryl lipid A derived from *Escherichia coli* (MPL; #L6638) was obtained from Sigma-Aldrich. 2F5 and 4E10 monoclonal antibodies were obtained through the NIH AIDS Research and Reference Reagent Program, Division of AIDS, NIAID, NIH from Dr. Hermann Katinger. Unless otherwise specified, all other reagents were obtained from Sigma-Aldrich.

i. Lipopeptide Synthesis

Peptides were synthesized on NovaPEG resin in an automated solid phase synthesizer (ABI 433A, Applied Biosystems, Foster City, Calif.) with standard fluorenylmethyloxycarbonyl/o-benzotriazole-N,N,N',N'-tetramethyl-uronium-hexafluoro-phosphate/n-hydroxybenzotriazole (FMOC/HBTU/HOBT) protocols. When appropriate, an orthogonally protected lysine (Fmoc-Lys(1-(4,4-Dimethyl-2,6-dioxo-cyclohexylidene)-3-methyl-butyl)-OH; Fmoc-Lys(ivDde)-OH) was incorporated at the C terminus for on-resin conjugation of lipids or biotin. The N terminus was generally Boc-protected unless the peptide was intended for N terminal modification, in which case Fmoc protection was utilized. Removal of the ivDde group was accomplished by 3×15 minute treatments of the peptidyl resin with 2% hydrazine hydrate in dimethylformamide (DMF; 10 mL per g resin). The resin was washed in DMF (3×10 mL) and dichloromethane (DCM; 3×10 mL) and dried under vacuum.

Nomenclature and structures of lipids used in this study are summarized in FIG. 1. Lipid conjugation was accomplished via amidation of a carboxylated lipid and a deprotected lysine ϵ-amine at the C terminus. For N terminal conjugation, lipids were attached directly to the deprotected N terminus. Several of the lipids contained carboxyl groups. In the case of DPG, PE, SM, and CL, a carboxyl group was introduced via reaction of an available alcohol (DPG, SM, CL) or amine (PE) with succinic anhydride. For DPG-Suc, 1.8 mmol DPG was dissolved in 5 mL anhydrous DCM and combined with 3.6 mmol succinic anhydride in 10 mL anhydrous pyridine. The mixture was refluxed at 60° C. overnight. For PE-Suc, 1.5 mmol PE was combined with 3 mmol succinic anhydride and 6 mmol triethylamine in 50 mL anhydrous chloroform ($CHCl_3$). The mixture was stirred at room temperature overnight. For CL-Suc, 80 μmol CL was combined with 400 μmol succinic anhydride and 400 μmol triethylamine in 5 mL anhydrous $CHCl_3$. The mixture was refluxed at 60° C. overnight. For SM-Suc, 136 μmol SM was combined with 684 μmol succinic anhydride and 684 μmol triethylamine in 5 mL anhydrous $CHCl_3$. The mixture was refluxed at 60° C. overnight. Reactions were continued to completion as monitored by thin layer chromatography (TLC) and matrix-assisted laser desorption/ionization mass spectrometry (MALDI-MS; Voyager DE, Applied Biosystems, Foster City, Calif.) in para-nitroaniline matrix. Products were washed twice with 1M hydrochloric acid (HCl), dried over sodium sulfate and stored dry until use. Carboxylated lipids were obtained in approximately 90-100% yield. Molecular weights and TLC $R_F$ values were as follows: DPG-Suc, 668.19 Da, $R_F$ 0.71 in 20:1 DCM:acetone; PE-Suc, 790.02 Da, $R_F$ 0.81 in 65:25:4 $CHCl_3$:MeOH:$NH_4OH$; CL-Suc, 1335.90 Da, $R_F$ 0.24 in 65:25:4 $CHCl_3$:MeOH:$NH_4OH$; SM-Suc, 767.83 Da, 826.62 Da, 853.02 Da, 910.78 Da, $R_F$ 0.66-0.79 in 65:25:4 $CHCl_3$:MeOH:$NH_4OH$. SM-Suc gave a series of peaks because the starting material was a natural product with a distribution of aliphatic chain lengths.

Lipidation was accomplished by activation of 270 μmol carboxylated lipid with 270 μmol each of HBTU, HOBT and diisopropylethylamine (DIEA) in anhydrous DMF/DCM (DCM as needed for lipid solubilization) for 30 min at room temperature followed by addition of 67.5 μmol resin and continued reaction under argon for 24 h at room temperature. Following the reaction, the resin was washed with DMF (4×10 mL) and DCM (4×10 mL) to remove unreacted lipids and dried under vacuum. Peptides were cleaved from the resin by treatment with trifluoroacetic acid containing 2.5% water, 2.5% ethanedithiol and 1% triisopropylsilane for 4 hours under argon. Cleaved peptides were precipitated into cold ethyl ether. The precipitate was pelleted by centrifugation at 3000 rpm (RT6000, Sorvall, Waltham, Mass.) and washed once with cold ethyl ether. The ether was poured off and the pellet was re-dissolved in methanol (MeOH), transferred to a round bottom flask, dried by rotary evaporation under reduced pressure and further dried under high vacuum. Lipopeptides were further separated from unconjugated peptide by reverse phase high pressure liquid chromatography (RP-HPLC; DX 500, Dionex, Sunnyvale, Calif.) on a semi-preparative C4 column (214TP510, Grace Vydac, Deerfield, Ill.) until unconjugated peptide was no longer detectable by MALDI-MS. Lipopeptide fractions were identified by MALDI-MS in 2,5-dihydroxybenzoic acid matrix, pooled and lyophilized. Stock lipopeptide solutions were prepared in MeOH or MeOH/$CHCl_3$ and stored at −20° C. Final yields were approximately 5-10%.

Biotinylated peptides were prepared for use in ELISA by an analogous method. Biotin was attached to the deprotected C terminal amine by activation of 500 μmol D-biotin with 500 μmol HBTU/HOBT/DIEA in 1.65 mL anhydrous 1:1 DMF/dimethylsulfoxide (DMSO) for 30 min followed by addition of resin and continued reaction under argon for 24 h at room temperature. Following the reaction, the resin was washed with 1:1 DMF/DMSO (3×10 mL), DMF (3×10 mL) and DCM (3×10 mL) and dried under vacuum. Biotinylated peptides were cleaved and purified as described above. Biotin content was quantified by 4'-hydroxyazobenzene-2-carboxylic acid dye exclusion (Sigma #H2153) according to the manufacturer's instructions.

ii. Liposome Preparation

Lipopeptides were formulated in liposomes composed of 15:2:3:0.3 DMPC:DMPG:Cholesterol:MPL. Prior to use, glassware was rinsed with MeOH and $CHCl_3$ and dried for at least 90 mM at 150° C. to destroy pyrogens. Lipid solutions were combined in borosilicate glass tubes and dried to a thin film by rotary evaporation under reduced pressure. Films were further dried under high vacuum overnight. Lipids were hydrated in sterile PBS (UCSF Cell Culture Facility) by intermittent vortexing and bath sonication under argon for a brief period (approximately 15 seconds) to disperse the lipids into the buffer. Defined diameter vesicles were formed by extrusion 11 times through 400 nm polycarbonate membranes using a hand-held extruder (Avestin, Ottowa, Canada). To prevent contamination, the extruder was disassembled and thoroughly cleaned with MeOH and sterile PBS between samples. The final formulation contained 1 mg/mL lipopeptide and 0.5 mg/mL monophosphoryl lipid A in 20 mM carrier lipid. Vesicle size was characterized by dynamic light scattering (Zetasizer 3000, Malvern, New Bedford, Mass.). Liposomes were stored at 4° C. under argon until use.

iii. Circular Dichroism

Liposomal lipopeptide samples were prepared as described above with the following modifications. Stock liposome solutions containing 5 mM carrier lipid and 500 μM lipopeptide were prepared in 10 mM phosphate, pH 7.4. To minimize light scattering, liposomes were prepared by bath sonication under argon until a size of less than 100 nm was obtained. For analysis, samples were diluted to 5 μM lipopeptide in 10 mM phosphate buffer containing 1 mM carrier lipid. Spectra were obtained with a J-715 spectrapolarimeter (Jasco, Easton, Md.) and data were processed using Jasco software. Data were acquired in continuous scanning mode with a pathlength of 1 cm, 0.1 nm interval and scan speed of 1 nm/s. Each spectrum represents an average of two scans. A background spectrum of "empty" liposomes in buffer was subtracted from each sample spectrum. Percent helicity was estimated from $\theta_{222}$ according to the method of Taylor and Kaiser.

iv. Tryptophan Fluorescence

Lipopeptide membrane partitioning was characterized by measurement of tryptophan fluorescence intensity as described with modifications. Briefly, DMPC:DMPG:Cholesterol liposomes were prepared in phosphate-buffered saline as described above. Lipopeptide stock solutions were prepared in MeOH. 12 nmol lipopeptide was injected via glass syringe (Hamilton, Reno, Nev.) into 1.2 mL buffer containing diluted liposomes (10-150 μM lipid). The samples were mixed by inversion and allowed to equilibrate in the dark at room temperature overnight. Fluorescence emission spectra were obtained on a SPEX Fluorolog spectrophotometer (Horiba Jobin Yvon, Edison, N.J.) with 1 cm pathlength, 2.5 mm excitation slit, 5.0 mm emission slit, 1 s integration time and 1 nm interval. For each liposome concentration, a background spectrum of "empty" liposomes in buffer was subtracted from the sample spectrum. Fluorescence intensity was determined by integration of the tryptophan fluorescence peak and data were normalized to the highest intensity in each sample series. Partition coefficients were calculated from the double reciprocal plot of normalized fluorescence intensity versus lipid concentration, according to the equation $F=(F_0*L*K_p)/(55.6+K_p*L)$ [29].

v. Animal Immunizations

All animal procedures were conducted in accordance with the policies and approval of the appropriate Institutional Animal Care and Use Committee. 8 week-old female BALB/C mice (Jackson Laboratories, Bar Harbor, Me.) were housed in a pathogen-free barrier facility. Animals received subcutaneous immunizations in alternating hind hocks on Days 0 and 14. Each injection contained 50 μg lipopeptide, 25 μg MPL and 1 μmol lipid vehicle in 50 μL sterile phosphate-buffered saline. On Day 28 blood was collected from the submandibular vein for characterization of antibody responses. Cells were removed by centrifugation at 14,000 rpm for 15 min (5415C, Eppendorf, Westbury, N.Y.) and sera were stored at −80° C. until use.

vi. ELISA

ELISAs were developed to quantify binding of immune sera to peptides, lipids, and recombinant gp140. Peptide ELISAs were conducted using MPR peptides biotinylated as described above and captured on 96 well streptavidin-coated plates (#15120, Pierce, Rockford, Ill.). Assays were performed according to the manufacturer's instructions with modifications. Biotinylated peptides were added to wells in PBS containing 0.1% Tween-20 (PBS-T) and incubated for 2 hr at 37° C. Following a wash step, sera were serially diluted in PBS containing 0.1% casein (C7078, Sigma-Aldrich) (PBS-C), added to wells and incubated for 30 min at 37° C. After reconstitution, horseradish peroxidase-conjugated secondary antibodies (IgG, IgG1, IgG2a; Jackson Immunoresearch, West Grove, Pa.) were diluted 1:1 in glycerol for long-term storage at −20° C. and further diluted 1:1000 in PBS-C immediately prior to use. Following a wash step, secondary antibodies were added to wells and incubated for 30 min at 37° C. Following a final wash step, a tetramethylbenzidine substrate solution (#T0440, Sigma-Aldrich) was added to wells and incubated for 30 min at room temperature. The reaction was stopped with 0.5M $H_2SO_4$ and the yellow product was monitored at 450 nm (Optimax, Molecular Devices, Sunnyvale, Calif.). All incubations were done in 100 μL volumes and wells were washed 6 times with PBS-T between each step. Titer was defined as the reciprocal dilution of immune sera yielding an optical density twice that of 1:200 preimmune sera after subtraction of background wells lacking serum. IgG1/IgG2a ratios were calculated as an average of optical density quotients measured at 3 dilutions after subtraction of background values. All samples were assayed in duplicate.

Lipid ELISAs were performed generally as follows. Lipids were diluted to 0.2 mg/mL in EtOH and 50 μL per well were added to flat-bottomed untreated polystyrene plates (Fisher) and allowed to dry overnight. Plates were blocked with 0.5% casein for 2 hr. After a wash step, immune sera were diluted 1:200 in 10% fetal bovine serum in PBS and incubated in wells for 1 hr. Wells were washed and peroxidase-conjugated anti-mouse IgG was diluted 1:1000 in PBS-C and added to wells for 1 hr. Following a wash step, plates were then read as indicated above. All incubations were done in 100 μL volumes at room temperature and wells were washed 6 times with PBS between each step.

Recombinant gp140 ELISAs were performed follows: Ba-1 gp140 (Immune Technology Corp, New York, N.Y.) was diluted to 5 μg/mL in 50 mM sodium carbonate, pH 9.6 and 100 μL per well were added to flat-bottomed high capacity immunoassay plates (Costar). Plates were sealed with parafilm and incubated at 4° C. overnight. Plates were blocked with 0.5% casein for 2 hr. After a wash step, immune sera were diluted 1:50 in PBS-C and incubated in wells for 1 hr. Wells were washed and peroxidase-conjugated anti-mouse IgG was diluted 1:1000 in PBS-C and added to wells for 30 min. Following a wash step, plates were then developed and read as indicated above. All incubations were done in 100 μL volumes at 37° C. and wells were washed 6 times with PBS-T between each step.

vii. Statistical Analysis

Statistical significance was assessed by analysis of variance and two-tailed Student's t test. Differences were considered significant if they exhibited p values <0.05 in the Student's t test. Data analyses were performed using Microsoft Excel and SigmaPlot.

B. Results i. Preparation and Analysis of Lipopeptides and Liposomes

This study sought to address the role of lipid structure in the humoral immune response to MPR lipopeptides formulated in liposomes. Three peptides were selected for lipid modification, corresponding to the 2F5 epitope (N-MPR), the 4E10 epitope (C-MPR) and an extended peptide spanning both epitopes (NC-MPR; summarized in FIG. 1). The sequences of N-MPR and C-MPR included flanking residues that were found to maximize binding affinities for their respective antibodies in vitro. Two helix-promoting isobutyric acid residues were incorporated into NC-MPR, as previously implemented in the design of a helically constrained 4E10 epitope peptide. The N terminus of NC-MPR was extended to include the full 2F5 epitope. An orthogonally protected lysine was included for lipid conjugation at the C terminus to mimic the native structure, in which the C terminus is anchored to the membrane.

Lipid anchors were selected to represent several basic lipid types: fatty acids, diacylglycerols, phospholipids and sterols. Additionally, some are implicated in cross-reactivity with 4E10 and 2F5 (cardiolipin) or in virus-cell fusion (virion lipid phosphatidylethanolamine; raft lipids sphingomyelin and cholesterol). Consideration was also given to lipid anchors that may facilitate elicitation of antibodies binding to both peptide and lipid moieties. Specifically, lipids lacking a phosphate (palmitic acid and diacylglycerol) were selected for comparison to phosphate-containing lipids because the phosphate and head group moieties are important in recognition by anti-phospholipid antibodies. Cholenic acid (CHOL) was chosen in addition to cholesterol hemisuccinate (CHEMS) due to work indicating that the 3β-hydroxyl is a primary moiety responsible for recognition of cholesterol by anti-cholesterol antibodies.

For those lipids lacking a carboxyl group, one was introduced by reaction with succinic anhydride. For peptide conjugation, the on-resin lipidation strategy allowed complete removal of unreacted lipid via extensive washing of the resin prior to cleavage. The remaining contaminant, unreacted peptide, was removed by RP-HPLC. Conjugated peptides were obtained in approximately 5-10% yield; steric hinderance in modification of the C terminal lysyl ϵ-amine and loss upon RP-HPLC purification may have contributed to the relatively poor yield. Human monoclonal antibodies 2F5 and 4E10 bound strongly to biotinylated MPR peptides containing their epitopes (N-MPR and C-MPR, respectively) by ELISA (FIG. 2). The cause for weak binding of 2F5 to C-MPR is uncertain but may be attributed to partial overlap in the peptide sequences. Regardless, sera of mice immunized with N-MPR lipopeptides did not bind to C-MPR by ELISA and vice versa. Liposomal formulation of MPR lipopeptides resulted in vesicles approximately 175-250 nm in diameter. Addition of peptide or lipopeptide did not appreciably affect vesicle size, with the exception of N-MPR-PE liposomes, which were slightly smaller than the others.

When formulated in liposomes, N-MPR secondary structure was greatly altered by the attached lipid moiety (FIG. 3*a*). Whereas attachment of CHEMS to N-MPR resulted in a modest increase in helicity (26.5% versus 20.7%), attachment of DPG substantially increased helical content (47.8% versus 20.7%). In contrast, attachment of CHEMS to NC-MPR only modestly affected its already helical conformation (FIG. 3*b*). For NC-MPR, the data suggest a trend in which C terminal attachment promotes helicity (8% and 5% respective increases when comparing 'C Terminus' versus 'Unconjugated' and 'Both Termini' versus 'N Terminus'), whereas N terminal attachment decreases helicity (2% and 5% respective decreases when comparing 'N Terminus versus 'Unconjugated' and 'Both Termini' versus 'C Terminus'). The NC-MPR spectra are in agreement with those reported for 4E10 epitope peptides with nearly identical C terminal helix restraints. By comparison, the lower overall helicity of NC-MPR may be attributed to the contribution of the extended N terminal segment not present in the peptide synthesized by Cardoso and coworkers.

Tryptophan fluorescence experiments revealed that the attached lipid moiety also affects partitioning of N-MPR into lipid bilayers (FIG. 4). Both PA and CHEMS conjugates exhibited incremental differences in tryptophan fluorescence as a function of liposome concentration. This indicates that as the concentration of liposomes is increased, additional lipopeptides partition into the membrane. However, tryptophan fluorescence of N-MPR-DPG was unaffected by increasing lipid concentration over the range measured. The $K_p$ of N-MPR-DPG was estimated to be at least an order of magnitude greater than that of N-MPR-PA or N-MPR-CHEMS ($5.84\times10^8$ versus $2.01\times10^7$ and $1.95\times10^7$, respectively). This observation suggests that N-MPR-DPG partitions more strongly into bilayer membranes than the other conjugates. Alternatively, the possibility that DPG promotes self-aggregation cannot be excluded. As hydrophobic bilayer environments are known to promote helicity of peptides, the increased helicity of N-MPR-DPG relative to N-MPR-CHEMS may correspond to increased membrane partitioning. Taken together, these data indicate that the attached lipid alters both the peptide's secondary structure and its behavior in bilayer vesicles.

ii. Response to Immunization

N-MPR lipid conjugates exhibited considerable differences in their ability to induce anti-peptide antibodies when administered to BALB/C mice (FIGS. 5 and 6). Sterols and lipids containing two or more acyl chains generally elicited anti-peptide titers in the range of $10^4$ to $10^5$. These lipopeptides elicited balanced IgG1/IgG2a responses, suggesting a balanced T helper response, with a slight preponderance of IgG1. Anti-peptide IgA responses were not detected in serum (data not shown). Unconjugated peptide formulated in liposomes induced a greater anti-peptide response (detected in 2 of 5 mice) than either palmitic acid or PC conjugates, both of which failed to elicit a detectable response. N-MPR-PC, in which the peptide was attached to the distal end of an acyl chain, may have functioned more as a single chain due to the distribution of polar groups (peptide and head group) throughout the molecule. Conjugation to CHEMS, but not DPG or CHOL, also elicited a weak response against the C-MPR peptide (FIG. 7).

Lipid reactivity of murine antisera was assayed because cross-reactivity of 2F5 and 4E10 with anionic phospholipids is thought to be important in their ability to neutralize HIV. The lipopeptide formulations did not elicit antibodies against either cardiolipin or phosphatidylglycerol but did evoke a weak response against cholesterol, which was negatively correlated with anti-peptide titers (Spearman rank order correlation $R=-0.853$, $p=0.0000002$). No difference in anti-cholesterol antibodies was detected between sera of mice that received the CHOL lipopeptide, in which the 3β-hydroxyl is available, and the CHEMS lipopeptide, in which the 3β-hydroxyl is masked. Cholesterol antibodies were likely generated by the unmodified cholesterol in the carrier formulation in addition to the lipopeptide itself. These assays were repeated with Tris-buffered saline to address concerns that the presence of soluble phosphate in the assay buffer may have inhibited anti-phospholipid antibody binding. However, phospholipid reactivity was also not detected in these assays (data not shown).

Figure 8:
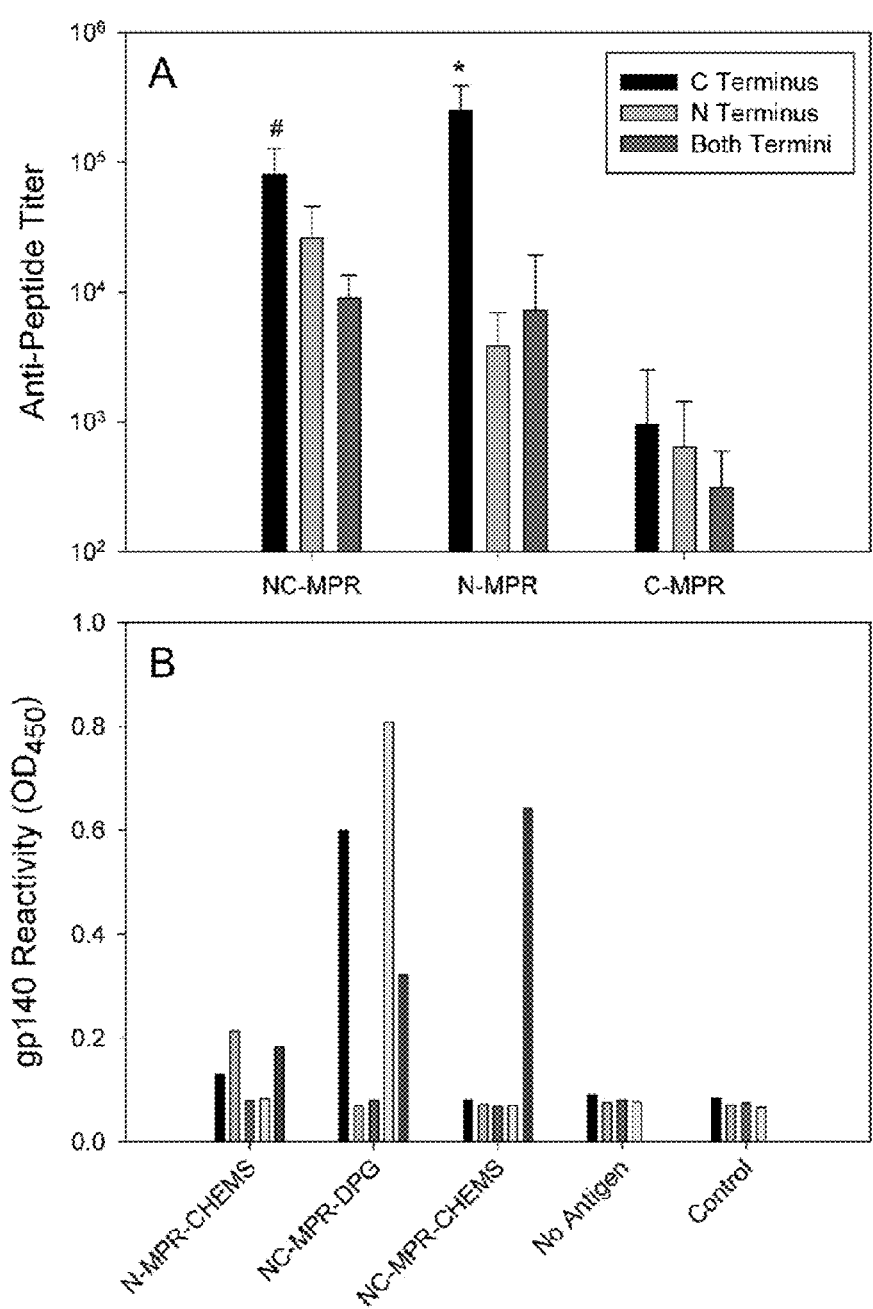

To further probe the utility of CHEMS conjugation for promoting the immunogenicity of the MPR, lipopeptides were synthesized in which CHEMS was attached to the C terminus, the N terminus, or both (FIG. 8a). All three molecules elicited antibodies that bound to the individual 2F5 and 4E10 epitopes (represented by N-MPR and C-MPR). Notably, the NC-MPR-CHEMS C terminal conjugate elicited a stronger response to N-MPR than to itself. The other two conjugates elicited significantly lower antibodies to N-MPR ($p<0.004$), suggesting that attachment of CHEMS to the N terminus diminished the antibody response to the N terminal segment of the peptide. However, conjugation to the C terminus exerted no detectable effect on the antibody response to the C terminal segment. None of the conjugates elicited detectable antibodies to cardiolipin or phosphatidylglycerol (data not shown).

Finally, we sought to determine if these conjugates could elicit antibodies that bind to recombinant gp140 (FIG. 8b). The gp140 construct used (Clade B, Strain Ba-1) differed from the MPR consensus sequence by only one residue (N677E). In control experiments, bnAb 2F5 and bnAb 4E10 bound strongly to this gp140 at 1 μg/mL (data not shown). Several immune sera bound weakly to gp140, but only at a very low dilution (1:50), suggesting that the majority of antibodies recognize structures other than that of the native protein. Although NC-MPR-DPG elicited greater reactivity to gp140 than NC-MPR-CHEMS (3/5 responders versus 1/5 responders), the reactivity is low and it is unclear if this difference is meaningful. Since the sequence of interest is positioned at the end of the C terminus of the recombinant construct, there was concern that adsorption on the ELISA plate may alter the structure and interfere with binding. However, binding was not stronger when the recombinant construct was attached to hexahistidine-binding plates via a hexahistidine tag (data not shown).

C. Discussion

The discovery of broadly neutralizing monoclonal antibodies reactive with the MPR region of gp41 from patient-derived cells raised the hope for an HIV vaccine against the epitopes recognized by these antibodies. Numerous studies of MPR-specific neutralizing antibodies suggest that presentation of MPR immunogens in a membrane environment could facilitate elicitation of neutralizing responses. However, recombinant viruses and MPR-transmembrane fusion constructs in lipid vesicles have not elicited high titer neutralizing antibodies.

We hypothesized that covalent attachment of lipid anchors to MPR segments would improve upon these approaches by increasing anti-peptide antibody titers, altering epitope structure within the membrane, or eliciting neutralizing antibodies. We compared sterols, fatty acids and phospholipids for promoting humoral responses to covalently attached antigens. The key finding of this study is that the structure of the lipid anchor exerts significant influence on the anti-peptide titer.

Unexpectedly, cholesterol hemisuccinate (CHEMS) promoted the greatest antibody response to an attached peptide, although the differences in immunogenicity were relatively small amongst the more potent anchors. CHEMS elicited significantly greater anti-peptide responses than cholenic acid (CHOL), a similar molecule (geometric mean titers of $5.3 \times 10^4$ and $1.8 \times 10^4$, respectively; $p=0.033$). Conjugation of CHEMS to the C terminus of the MPR promoted significantly greater anti-peptide responses than did conjugation of CHEMS to the N terminus ($p<0.05$). The two lipid-anchored NC-MPR peptides tested also elicited antibodies that bound weakly to gp140 by ELISA.

No single factor, such as position of the lipid anchor, peptide helical content, lipopeptide partition coefficient, or presence of phosphate on the anchor determined the ability of a lipopeptide to elicit anti-peptide antibodies. However, the N terminal portion of the MPR (containing the 2F5 epitope) was considerably more immunogenic in BALB/C mice than the C terminal segment (containing the 4E10 epitope). For unstructured peptides, lipid conjugation may be used to manipulate secondary structure of peptides within membranes. Thus, these lipids augment the toolbox available to HIV-1 vaccine researchers for probing MPR immunogenicity and designing MPR-targeted vaccines.

Our strategy is analogous to that reported by Giannecchini and colleagues, in which octadecanoic acid was attached to the C terminus of MPR of feline immunodeficiency virus. However, this immunogen elicited only weak anti-peptide antibodies (ELISA OD<1.0 at 1:100 serum dilution) in cats. Thus, there is a need for immunogens that not only target the appropriate antigenic structure, but also elicit high titer antibodies. Coutant and coworkers also recently derivatized an MPR peptide with phosphatidylethanolamine to probe its physiological structure within membranes, but did not report antibody titers. Our findings suggest that lipid-anchored MPR peptides are highly immunogenic in mice; the titers are an order of magnitude higher than those reported by Lenz and colleagues in BALB/C mice immunized with liposome-anchored trimeric gp41.

The use of liposomes containing monophosphoryl lipid A (MPL) for induction of antibody and cytotoxic T lymphocyte responses against liposome-associated peptides and proteins has been pioneered by Alving and colleagues. Adjuvant mechanisms attributed to liposomes containing MPL include enhanced uptake, processing and presentation by antigen presenting cells, prolonged persistence at the injection site and activation of innate immunity through ligation of Toll-like receptor 4. Incorporation of MPL into liposomes also reduces reactogenicity while maintaining adjuvant activity. Moreover, several studies have demonstrated that covalent attachment of peptides to liposomes enhances humoral immune responses to liposome-associated peptides and proteins. As compared to non-covalent encapsulation, White and colleagues demonstrated increased antibody responses to a peptide derived from the V3 loop of gp120 when the peptide was acylated at the N terminus prior to liposome formulation or attached via a reversible disulfide bond to liposomes containing a thiolated cholesterol derivative. Liposomes adjuvanted with MPL have also been used to elicit anti-lipid antibodies of diverse specificities. A murine monoclonal antibody to phosphatidylinositol phosphate with no known HIV-1 binding specificity has also been shown to neutralize primary isolates, suggesting that membrane binding alone may be sufficient for neutralization.

The failure to elicit anti-phospholipid antibodies in the present study is at odds with a recent report in which immunization of BALB/C mice with a liposome-associated peptide adjuvanted by MPL elicited dual specificity, low titer (O.D. ~1.0 at 1:00 serum dilution) antibodies that recognized both peptide and lipid determinants. In these studies the MPR sequence was modified with a universal T helper epitope from tetanus toxin but did not contain a covalent lipid. As induction of anti-lipid antibodies by liposomes is affected by a number of factors, including formulation and injection route, modulation of these parameters in future studies may enable MPR lipopeptides presented here to elicit lipid cross-reactive antibodies.

It is unclear why a sterol-anchored peptide would be more immunogenic than a peptide anchored by aliphatic chains. The mechanism does not appear to arise from induced changes in secondary structure; N-MPR-CHEMS, which differed little from free N-MPR peptide by circular dichroism, elicited nearly an order of magnitude higher geometric mean titer (GMT) than N-MPR-DPG ($5.3\times10^4$ and $6.7\times10^3$, respectively), which exhibited considerably greater helical content (26.5% and 47.8%, respectively). Membrane partitioning does not explain the disparity in anti-peptide titers either, as N-MPR-DPG partitioned much more strongly into liposomes than N-MPR-CHEMS ($K_p>5.84\times10^8$ and $K_p=1.95\times10^7$). Moreover, although N-MPR-CHEMS and N-MPR-PA exhibited very similar partitioning behavior, N-MPR-PA failed to elicit any detectable peptide antibodies. Thus, the adjuvant activity of sterol conjugates arises from some other mechanism. CHEMS conjugates may adopt a more highly exposed surface structure than CHOL, DPG, or other less immunogenic lipopeptides. However, efforts to quantitate liposome surface accessibility of lipid-modified MPR peptides are complicated by the ability of the 2F5 and 4E10 antibodies to intercalate into the membrane and "extract" their epitopes. Alternatively, the lipid moiety may alter the processing of associated T helper epitopes or facilitate membrane transfer to cells that provide more efficient presentation to B lymphocytes.

Several of the findings reported here may prove useful in studies of the MPR as a target for design of immunogens that elicit neutralizing antibodies. First, the data bolster the assertion that the immunogenicity of the MPR arises predominantly from the N terminal portion. This fact was borne out through immunization studies with peptides containing only a single epitope (N-MPR and C-MPR) or both epitopes (NC-MPR). N-MPR-CHEMS elicited an anti-N-MPR GMT of $5.3\times10^4$ whereas C-MPR-CHEMS elicited anti-C-MPR titers of less than $6\times10^2$. Additionally, mice immunized with NC-MPR derivatized with CHEMS at the C terminus generated extremely high titers (GMT $2.5\times10^5$) against the N terminal region of the peptide but only low titers against the C terminal segment (GMT $9\times10^2$). The poor immunogenicity of the 4E10 epitope may arise from masking of the epitope within the membrane, as is predicted to occur in native envelope spikes. However, other studies indicate that the peptide sequence itself is poorly immunogenic. If this is due to autoantigen mimicry, more potent adjuvants may be needed to circumvent a peripheral tolerance barrier.

The lipopeptide immunogens described here may be useful in a prime-boost immunization regimen for focusing the immune response to the MPR. First, the immune system would be primed with highly immunogenic, membrane-bound peptides that induce antibody responses targeted to MPR peptides in the context of membrane, minimizing antibodies directed against other immunodominant, non-neutralizing envelope determinants. Second, the immune system would be boosted with a recombinant construct in which the MPR is constrained in the appropriate structural confirmation. Thus, only MPR-reactive antibodies of the appropriate confirmation would be boosted, minimizing antibodies directed against irrelevant MPR structures.

An important observation is that the α-helicity of unstructured MPR peptides can be modulated through alteration of the attached lipid moiety. Additionally, attachment of the lipid anchor to the C terminus produced a more potent immunogen than did attachment of the anchor to the N terminus. Finally, the results indicate that cholesterol hemisuccinate is a simple but effective lipid anchor for creating lipopeptide immunogens.

D. References

Karlsson Hedestam G, Fouchier R, Phogat S, Burton D, Sodroski J, Wyatt R. The challenges of eliciting neutralizing antibodies to HIV-1 and to influenza virus. Nature Reviews Microbiology 2008; 6(2):143-55.

Salzwedel K, Johnston P, Roberts S, Dubay J, Hunter E. A conserved tryptophan-rich motif in the membrane-proximal region of the human immunodeficiency virus type 1 gp41 ectodomain is important for Env-mediated fusion and virus infectivity. Journal of Virology 1999; 73(3):2469-80.

Zwick M B, Labrijn A F, Wang M, Spenlehauer C, Saphire E O, Binley J M, et al. Broadly neutralizing antibodies targeted to the membrane-proximal external region of human immunodeficiency virus type 1 glycoprotein gp41. Journal of Virology 2001; 75(22):10892-905.

Montero M, van Houten N, Wang X, Scott J. The membrane-proximal external region of the human immunodeficiency virus type 1 envelope: dominant site of antibody neutralization and target for vaccine design. Microbiology and Molecular Biology 2008; 72(1):54-85.

Shibli D J, Montelaro R C, Vogel H J. The membrane-proximal tryptophan-rich region of the HIV glycoprotein, gp41, forms a well defined helix in dodecylphosphocholine micelles. Biochemistry 2001; 40:9570-78.

Chan D, Fass D, Berger J, PS K. Core structure of gp41 from the HIV envelope glycoprotein. Cell 1997; 89(2):263-73.

Cardoso R M F, Zwick M B, Stanfield R L, Kunert R, Binley J M, Katinger H, et al. Broadly neutralizing anti-HIV antibody 4E10 recognizes a helical conformation of a highly conserved fusion-associated motif in gp41. Immunity 2005; 22(2):163-73.

Ofek G, Tang M, Sambor A, Katinger H, Mascola J R, Wyatt R, et al. Structure and mechanistic analysis of the anti-human immunodeficiency virus type 1 antibody 2F5 in complex with its gp41 epitope. Journal of Virology 2004; 78(19):10724-37.

Liang X, Munshi S, Shendure J, Mark III G, Davies M, Freed D, et al. Epitope insertion into variable loops of HIV-1 gp120 as a potential means to improve immunogenicity of viral envelope protein. Vaccine 1999; 17(22):2862-72.

Law M, Cardoso R M, Wilson I A, Burton D R. Antigenic and immunogenic study of membrane-proximal external region-grafted gp120 antigens by a DNA prime-protein boost immunization strategy. Journal of Virology 2007; 81(8):4272-85.

McGaughey G, Barbato G, Bianchi E, Freidinger R, Garsky V, Hurni W, et al. Progress towards the development of a HIV-1 gp41-directed vaccine. Current HIV Research 2004; 2:193-204.

Davis K, Bibollet-Ruche F, Li H, Decker J, Kutsch 0, Morris L, et al. HIV-2/HIV-1 envelope chimeras detect high titers of broadly reactive HIV-1 V3-specific antibodies in human plasma. Virology 2008; doi:10.1128/JVI.01743-08.

Garrity R, Rimmelzwaan G, Minassian A, Tsai W, Lin G, de Jong J, et al. Refocusing neutralizing antibody response by targeted dampening of an immunodominant epitope. Journal of Immunology 1997; 159(1):279-89.

Alam S M, Scearce R M, Parks R J, Plonk K, Plonk S G, Sutherland L L, et al. Human immunodeficiency virus type 1 gp41 antibodies that mask the membrane proximal region epitopes: antibody binding kinetics, induction, and potential for regulation in acute infection. Journal of Virology 2008; 82(1):115-25.

Penn-Nicholson A, Han D, Kim S, Park H, Ansari R, Montefiori D C, et al. Assessment of antibody responses against gp41 in HIV-1 infected patients using soluble gp41 fusion proteins and peptides derived from M group consensus envelope. Virology 2008; 372(2):442-56.

Alam S M, McAdams M, Boren D, Rak M, Scearce R M, Gao F, et al. The role of antibody polyspecificity and lipid reactivity in binding of broadly neutralizing anti-HIV-1-envelope human monoclonal antibodies 2F5 and 4E10 to glycoprotein 41 membrane proximal envelope epitopes. Journal of Immunology 2007; 178(7):4424-35.

Haynes B F, Fleming J, St Clair E, Katinger H, Stiegler G, Kunert R, et al. Cardiolipin polyspecific autoreactivity in two broadly neutralizing HIV-1 antibodies. Science 2005; 208 (5730):1906-08.

Vcelar B, Stiegler G, Wolf H M, Muntean W, Leschnik B, Mehandru S, et al. Reasessment of autoreactivity of the broadly neutralizing HIV antibodies 4E10 and 2F5 and retrospective analysis of clinical safety data. AIDS 2007; 21(16):2161-70.

Matyas G, Beck Z, Karasavvas N, Alving C R. Lipid binding properties of 4E10, 2F5, and WR304 monoclonal antibodies that neutralize HIV-1. Biochimica et Biophysica Acta 2008;Published Online Dec. 3, 2008:doi:10.1016/j.bbamem.2008.11.015.

Sun Z Y, Oh K J, Kim M, Yu J, Brusic V, Song L, et al. HIV-1 broadly neutralizing antibody extracts its epitope from a kinked gp41 ectodomain region on the viral membrane. Immunity 2008; 28(1):52-63.

Lenz O, Dittmar M, Wagner A, Ferko B, Vorauer-Uhl K, Stiegler G, et al. Trimeric membrane-anchored gp41 inhibits HIV membrane fusion. Journal of Biological Chemistry 2005; 280(6):4095-101.

Luo M, Yuan F, Liu Y, Jiang S, Song X, Jiang P, et al. Induction of neutralizing antibody against human immunodeficiency virus type 1 (HIV-1) by immunization with gp41 membrane-proximal external region (MPER) fused with porcine endogenous retrovirus (PERV) p15E fragment. Vaccine 2006; 24(4):435-42.

Ye L, Sun Y, Lin J, Bu Z, Wu Q, Jiang S, et al. Antigenic properties of a transport-competent influenza HA-HIV Env chimeric protein. Virology 2006; 352(1):74-85.

Huarte N, Lorizate M, Kunert R, Nieva J L. Lipid modulation of membrane-bound epitope recognition and blocking by HIV-1 neutralizing antibodies. FEBS Letters 2008; 582 (27):3798-804.

White W I, Cassatt D R, Madsen J, Burke S J, Woods R M, Wassef N M, et al. Antibody and cytotoxic T-lymphocyte responses to a single liposome-associated peptide antigen. Vaccine 1995; 13(12):1111-22.

Fujii G, Ernst W, Adler-Moore J. The VesiVax system: a method for rapid vaccine development. Frontiers in Bioscience 2008; 13:1968-80.

Taylor J, Kaiser E. Structure-function analysis of proteins through the design, synthesis, and study of peptide models. Methods of Enzymology 1987; 154:473-98.

Chattopadhyay A, Mukherjee S, Rukmini R, Rawat S, Sudha S. Ionization, partitioning, and dynamics of tryptophan octyl ester: Implications for membrane-bound tryptophan residues. Biophysical Journal 1997; 73(2):839-49.

Huang Z, Haugland R. Partition coefficients of fluorescent probes with phospholipid membranes. Biochemical and Biophysical Research Communications 1991; 181(1):166-71.

Kamala T. Hock immunization: A humane alternative to mouse footpad injections. Journal of Immunological Methods 2007; 328(1-2):204-14.

Diaz C, Balasubramanian K, Schroit A J. Synthesis of disulfide-containing phospholipid analogs for the preparation of head group-specific lipid antigens: Generation of phosphatidylserine antibodies. Bioconjugate Chemistry 1998; 9(2):250-54.

Brunel F M, Zwick M B, Cardoso R M, Nelson J D, Wilson I A, Burton D R, et al. Structure-function analysis of the epitope for 4E10, a broadly neutralizing human immunodeficiency virus type 1 antibody. Journal of Virology 2006; 80(4):1680-87.

Cardoso R M F, Brunel F M, Ferguson S, Zwick M, Burton D R, Dawson P E, et al. Structural basis of enhanced binding of extended and helically constrained peptide epitopes of the broadly neutralizing HIV-1 antibody 4E10. Journal of Molecular Biology 2007; 365(5):1533-44.

Brugger B, Glass B, Haberkant P, Leibrecht I, Wieland F, Krausslich H. The HIV lipidome: A raft with an unusual composition. Proceedings of the National Academy of Sciences 2006; 103(8):2641-46.

Liao Z, Graham D, Hildreth J. Lipid rafts and HIV pathogenesis: virion-associated cholesterol is required for fusion and infection of susceptible cells. AIDS Research and Human Retroviruses 2003; 19(8):675-87.

Alving C, Rao M. Lipid A and liposomes containing lipid A as antigens and adjuvants. Vaccine 2008; 26(24):3036-45.

Dijkstra J, Swartz G M, Raney J J, Aniagolu J, Toro L, Nacy C A, et al. Interaction of anti-cholesterol antibodies with human lipoproteins. Journal of Immunology 1996; 157(5): 2006-13.

Biro A, Cervenak L, Balogh A, Lorincz A, Uray K, Horvath A, et al. Novel anti-cholesterol monoclonal immunoglobulin G antibodies as probes and potential modulators of membrane raft-dependent immune functions. Journal of Lipid Research 2007; 48(1):19-29.

Alfsen A, Bomsel M. HIV-1 gp41 envelope residues 650-685 exposed on native virus act as a lectin to bind epithelial cell galatosyl ceramide. Journal of Biological Chemistry 2002; 277(28):25649-59.

Li S, Deber C. Peptide environment specifies conformation. Helicity of hydrophobic segments compared in aqueous, organic, and membrane environments. Journal of Biological Chemistry 1993; 268(31):22975-78.

Locksley R, Scott P. Helper T-cell subsets and cytokines in mouse leishmaniasis: induction, expansion and effector function. Immunology Today 1991; 12(3):A58-A61.

Haynes B F, Alam S M. HIV-1 hides an Achilles' heel in virion lipids. Immunity 2008; 28(1):10-12.

Banerji B, Lyon J, Alving C. Membrane lipid composition modulates the binding specificity of a monoclonal antibody against liposomes. Biochemica et Biophysica Acta 1982; 689 (2):319-29.

Sathaliyawala T, Rao M, Maclean D M, Birx D L, Alving C R, Rao V B. Assembly of human immunodeficiency virus (HIV) antigens on bacteriophage T4: a novel in vitro approach to construct multicomponent HIV vaccines. Journal of Virology 2006; 80(15):7688-98.

Muster T, Guinea R, Trkola A, Purtscher M, Klima A, Steindl F, et al. Cross-neutralizing activity against divergent human immunodeficiency virus type 1 isolates induced by the gp41 sequence ELDKWAS. Journal of Virology 1994; 68(6): 4031-34.

Marusic C, Rizza P, Lattanzi L, Mancini C, Spada M, Belardelli F, et al. Chimeric plant virus particles as immunogens for inducing murine and human immune responses against human immunodeficiency virus type 1. Journal of Virology 2001; 75(18):8434-39.

Zhang H, Huang Y, Fayad R, Spear G, Qiao L. Induction of mucosal and systemic neutralizing antibodies against human immunodeficiency virus type 1 (HIV-1) by oral immunization with bovine papillomavirus-HIV-1 gp41 chimeric virus-like particles. Journal of Virology 2004; 78(15):8342-48.

Giannecchini S, D'Ursi A, Esposito C, Scrima M, Zabogli E, Freer G, et al. Antibodies generated in cats by a lipopeptide reproducing the membrane-proximal external region of the feline immunodeficiency virus transmembrane enhance virus infectivity. Clinical and Vaccine Immunology 2007; 14(8):944-51.

Coutant J, Yu H, Clement M, Alfsen A, Toma F, Curmi P, et al. Both lipid environment and pH are critical for determining physiological solution structure of 3-D-conserved epitopes of the HIV-1 gp41-MPER peptide P1. FASEB Journal 2008; 22(12):4338-51.

Alving C. Liposomes as carriers of antigens and adjuvants. Journal of Immunological Methods 1991; 140(1):1-13.

Karasavvas N, Beck Z, Tong J, Matyas G R, Rao M, McCutchan F E, et al. Antibodies induced by liposomal protein exhibit dual binding to protein and lipid epitopes. Biochemical and Biophysical Research Communications 2008; 366(4):982-87.

Verma J, Rao M, Amselem S, Krzych U, Alving C, Green S, et al. Adjuvant effects of liposomes containing lipid A: Enhancement of liposomal antigen presentation and recruitment of macrophages. Infection and Immunity 1992; 60(6):2438-44.

Alving C R, Koulchin V, Glenn G, Rao M. Liposomes as carriers of peptide antigens: Induction of antibodies and cytotoxic T lymphocytes to conjugated and unconjugated peptides. Immunological Reviews 1995; 145:5-31.

Dal Monte P, Szoka Jr F. Antigen presentation by B cells and macrophages of cytochrome c and its antigenic fragment when conjugated to the surface of liposomes. Vaccine 1989; 7(5):401-08.

Yokochi T, Inoue Y, Yokoo J, Kimura Y, Kato N. Retention of bacterial lipopolysaccharide at the site of subcutaneous injection. Infection and Immunity 1989; 57(6):1786-91.

Miller S, Ernst R, Bader M. LPS, TLR4 and infectious disease diversity. Nature Reviews Microbiology 2005; 3(1):36-46.

Dijkstra J, Mellors J, Ryan J, Szoka F C. Modulation of the biological activity of bacterial endotoxin by incorporation into liposomes. Journal of Immunology 1987; 138(8):2663-70.

Fernandes I, Frisch B, Muller S, Schuber F. Synthetic lipopeptides incorporated in liposomes: in vitro stimulation of the proliferation of murine splenocytes and in vivo induction of an immune response against a peptide antigen. Molecular Immunology 1997; 34(8-9):569-76.

Frisch B, Muller S, Briand J, Van Regenmortel M, Schuber F. Parameters affecting the immunogenicity of a liposome-associated synthetic hexapeptide antigen. European Journal of Immunology 1991; 21(1):185-93.

Friede M, Muller S, Briand J, Plaue S, Fernandes I, Frisch B, et al. Selective induction of protection against influenza virus infection in mice by a lipid-peptide conjugate delivered in liposomes. Vaccine 1994; 12(9):791-97.

Brown B K, Karasavvas N, Beck Z, Matyas G, Birx D L, Polonis V R, et al. Monoclonal antibodies to phosphatidylinositol phosphate neutralize human immunodeficiency virus type 1: role of phosphate-binding subsites. Journal of Virology 2007; 81(4):2087-91.

Beck Z, Karasavvas N, Matyas G, Alving C R. Membrane-specific antibodies induced by liposomes can simultaneously bind to HIV-1 protein, peptide, and membrane lipid epitopes. Journal of Drug Targeting 2008; 16(7-8):535-42.

Schuster B, Neidig M, Alving B, Alving C. Production of antibodies against phosphocholine, phosphatidylcholine, sphingomyelin, and lipid A by injection of liposomes containing lipid A. Journal of Immunology 1979; 122(3):900-05.

Banerji B, Kenny J, Scher I, Alving C. Antibodies against liposomes in normal and immune-defective mice. Journal of Immunology 1982; 128(4):1603-07.

Robinson J, Case M, Brooks C. Palmitic acid conjugation of a protein antigen enhances major histocompatibility complex class II-restricted presentation to T cells. Immunology 1992; 76(4):593-98.

Hosmalin A, Andrieu M, Loing E, Desoutter J, Hanau D, Gras-Masse H, et al. Lipopeptide presentation pathway in dendritic cells. Immunology Letters 2001; 79(1-2):97-100.

Frey G, Peng H, Rits-Volloch S, Morelli M, Cheng Y, Chen B. A fusion-intermediate state of HIV-1 gp41 is targeted by broadly neutralizing antibodies. Proceedings of the National Academy of Sciences 2008; 105(10):3739-44.

EXAMPLE 2

Synthesis of Amine-derivatized Sterol Derivative (Chol-amine)

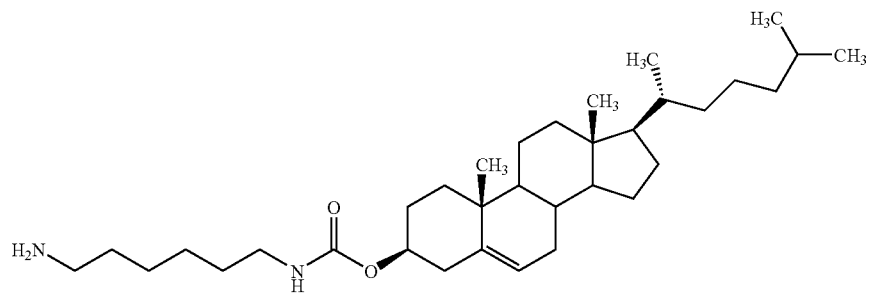 [SMILES: CC(C)CCC[C@@H](C)[C@H]1CCC2C3CC=C4C[C@@H](OC(=O)NCCCCCCN)CC[C@]4(C)C3CC[C@@]21C]

In the following example, the following abbreviations are used: Methanol (MeOH); Isopropyl alcohol (IPA); Tetrabutylammonium chloride (TBAC); Dichloromethane ($CH_2Cl_2$); Cholesteryl chloroformate (Chol-CF); Hexanediamine (HDA); Tetraethylammonium chloride (TEAC).

Typically, a 1 g synthesis was performed in a 1:1 ratio of chol-CF to HDA. 1 g (2.23 mmoles) of chol-CF was dissolved in 5 mL of CH$_2$Cl$_2$, and added dropwise into 258.8 mg (2.23 mmoles) of HDA dissolved in 5 mL of MeOH. The reaction was stirred at room temperature, no incubation time is required. 20 mL of MeOH and 2.5 mL of CH$_2$Cl$_2$ was added to the crude product (10 mL). The clear solution was then loaded onto a HyperSil C18 column (10 g, Thermo Scientific) pre-wet with ~30 ml of MeOH. The flow through was collected in 5 mL fractions (8 mL first fraction, 5 mL thereafter). The column was then washed with 20 mL of MeOH, and the wash fractions were also collected in increments of 5 mL. Fractions containing pure compound were combined and dried using a rotary evaporator. The dried product was dissolved in 75:25, MeOH:CH$_2$Cl$_2$, and stored at room temperature until use.

HPLC analysis. Analysis of product was performed using a Dionex GP50 HPLC system. Separation of lipid components were accomplished on a C18 column (Dionex Acclaim 120, 5 µm, 120 A, 4.6×250 mm) using isocratic elution with MeOH:IPA (25:75 v/v) containing 100 mM TEAC, pH 7.8 (1 ml/min flow rate; 25° C.). Detection was by 205 nm absorbance using a Dionex PDA-100 photodiode array detector. Typically, lipid samples were dissolved in MeOH: CH$_2$Cl$_2$ and 20 µL analyzed.

EXAMPLE 3

Synthesis of Maleimide-derivatized Sterol Derivative (Chol-Maleimide)

In the following example, the following abbreviations are used: Dichloromethane (CH$_2$Cl$_2$); Methanol (MeOH); Chol-amine (CA); Tetrabutylammonium chloride (TBAC); N-[ε-maleimidocaproyloxy]succinimide ester (EMCS).

Chol-amine was prepared at 20 mg/ml in MeOH: CH$_2$Cl$_2$ (1:1 v/v). EMCS was prepared at 11.6 mg/ml in MeOH: CH$_2$Cl$_2$ (1:1 v/v). The reaction was initiated by addition of one volume of EMCS to one volume of chol-amine. The mixture was incubated 60 min, 25° C., with stifling. This reaction can be scaled accordingly.

Purification of chol-maleimide. The Dionex UltiMate 3000 HPLC system was employed for preparative scale purification of chol-maleimide. 2 ml of the chol-maleimide reaction mixture, equivalent to approximately 15 mg of materials, was injected and components separated by isocratic elution with methanol containing 0.0025% acetic acid on a preparative C18 column (Grace Alltima; 22×250 mm; 5 µm; PN 81105); flow rate 10 ml/min; 205 nm detection. Chol-maleimide eluted as a peak at approximately 30-35 min. The chol-maleimide fractions were collected and chilled at −20 C for 30 min, then lyophilized 48 hr to obtain dry purified chol-maleimide.

HPLC analysis. Analysis of lipids was performed using a Dionex GP50 HPLC system. Separation of lipid components were accomplished on a C18 column (Dionex Acclaim 120, 5 µm, 120 A, 4.6×250 mm) using isocratic elution with MeOH:IPA (90:10 v/v) containing 100 mM TEAC, pH 7.8 (1 ml/min flow rate; 25° C.). Detection was by 205 nm absorbance using a Dionex PDA-100 photodiode array detector. Typically, lipid samples were dissolved in MeOH:CH$_2$Cl$_2$ (7:1 v/v) and 20 µL analyzed.

EXAMPLE 4

Poly-γ-D-glutamic Acid (PGA) as an Antigen to Form Liposomal Vaccines Against *Bacillus* Species A. Materials. Dichloromethane (CH$_2$Cl$_2$; Honeywell # AH300-4). Acetic Acid (HOAc; EM Science # AX0074-6). Sodium phosphate, monobasic (NaH2PO4; Fisher Scientific # S369-3). Sodium phosphate, dibasic (Na2HPO4; Fisher Scientific # S471-3). Di-myristoyl phosphatidyl choline (DMPC; Lipoid # 562207-1/10). Di-myristoyl phosphatidyl glycerol (DMPG; NOF # GM030805). Cholesterol (NOF # 70721). Chol-maleimide (Molecular Express Inc.). Mono-phosphoryl lipid A (MPL; Sigma-Aldrich # L6895). Poly-D-glutamic acid (PGA; Anaspec Inc. #59898).

B. Formation of liposomes. Chol-maleimide liposome formulations are shown in Table I.

| Component | Amount (mg) | MW | Concentration [mg/ml] | Concentration [mmole/ml] | Mole Ratio |
| --- | --- | --- | --- | --- | --- |
| DMPC | 825.20 | 678.00 | 41.26 | 0.0609 | 15.00 |
| DMPG | 162.09 | 665.90 | 8.10 | 0.0122 | 3.00 |
| Cholesterol | 46.69 | 386.70 | 2.33 | 0.0060 | 1.49 |
| CMI | 30.00 | 722.05 | 1.50 | 0.0021 | 0.51 |
| MPL | 6.00 | | 0.30 | | |

Briefly, dry lipid mixtures in quantities shown in Table I, without or with MPL, were dissolved in 10 ml of CH$_2$CL$_2$ in 250 ml glass round bottom flasks. Lipid films were formed by evaporation of the CH$_2$CL$_2$ using a Yamato RE600 rotary evaporator (20 rpm, 25° C., 1 hr). Films were maintained under vacuum for an additional 24 to 48 hr to ensure complete evaporation of solvents. Dried films were hydrated by addition of 20 ml of 10 mM sodium phosphate buffer, pH 7.0, with rotary agitation by the Yamato RE600 rotary evaporator (20 rpm, 25° C., no vacuum, 30-60 min). Liposomes were formed by microfluidization of the hydrated films using a Microfluidics M-110L microfluidizer (F20Y-75 µL chamber; 11,000 psi; 25° C.; 3 passes). Subsequent flushing of the microfluidizer with an addition 40 ml of 10 mM sodium phosphate buffer, pH 7.0 (to recover excess liposomes remaining in the microfluidizer) yielded a total crude liposome sample of approximately 60 ml. Crude liposomes were concentrated by ultra-filtration (Amicon system, Millipore BPMK04310 membrane; 40 psi; 25° C.) to approximately 15 ml and sterilized by filtration through 0.22 µm PES membrane syringe filtration units (Millipore Millex-GP filter units; SLGP033RS). Samples were analyzed by HPLC to determine the concentrations of the lipid components. Based on HPLC analysis, sterilized concentrated crude liposomes were diluted to 2× working concentration with sterilized 10 mM sodium phosphate buffer, pH 7.0. Table I shows the 2× formulation and concentration of each lipid component.

C. HPLC analysis of lipids. Analysis of lipid components was performed using a Dionex GP50 HPLC system. Separation of lipid components were accomplished on a C18 column (Dionex Acclaim 120, 5 µm, 120 A, 4.6×250 mm) using isocratic elution with MeOH:IPA (90:10 v/v) containing 100 mM TEAC, pH 7.8 (1 ml/min flow rate; 25° C.). Detection was by 205 nm absorbance using a Dionex PDA-100 photodiode array detector. Typically, samples were prepared by dissolving 100 µL of liposome in 400 uL of MeOH:$CH_2Cl_2$ (7:1 v/v) and 20 µL of dissolved samples were analyzed.

D. Analysis of liposome size. Liposome size analysis was performed using a Microtrac—UPA150 particle size analyzer blanked with 10 mM sodium phosphate buffer, pH 7.0 (3 min detection time). Liposome samples were typically diluted to approximately 0.3× working concentration for particle size analysis.

E. Formation of PGA Liposome. PGA was prepared at 0.3 mg/ml in 10 mM sodium phosphate buffer, pH 7.0. Conjugation of PGA to chol-maleimide liposome was initiated by addition of 1 volume of PGA to 1 volume of 2× Chol-maleimide liposomes (with or without MPL). Table II outlines the conjugation scheme for various samples prepared. CMI=cholesterol maleimide; L-CMI=chol-maleimide-containing liposome.

| Sample | Lot Number | L-CMI (2X) | L-CMI + MPL (2X) | PGA (0.3 mg/ml) | Buffer (10 mM NaPi) |
|---|---|---|---|---|---|
| Buffer | 080808A | | | | 6 ml |
| L-CMI | 080808B | 3 ml | | | 3 ml |
| L-CMI + MPL | 080808C | | 3 ml | | 3 ml |
| L-CMI + PGA | 080808D | 3 ml | | 3 ml | |
| L-CMI + MPL + PGA | 080808E | | 3 ml | 3 ml | |

After 1 hr incubation at 25° C., each reaction mixture was washed with 10 mM sodium phosphate buffer, pH 7.0, by Amicon ultra-filtration to approximately 100 fold dilution to remove any excess PGA. Washed PGA liposomes were filter sterilized, analyzed by HPLC, then diluted to 1× lipid concentration similarly as described above.

F. HPLC analysis of PGA. Analysis of PGA was performed using a Dionex GP50 HPLC system. Separation and elution of PGA was accomplished on a C8 column (Dionex Acclaim 120, 5 µm, 120 A, 4.6×250 mm) using isocratic elution with 10% acetonitrile containing 0.1% TFA (1 ml/min flow rate; 25° C.). Detection was by 220 nm absorbance using a Dionex PDA-100 photodiode array detector. Typically, samples were prepared by dissolving 100 µL of liposome in 400 µL of MeOH:$CH_2Cl_2$ (7:1 v/v) and 20 µL of dissolved samples were analyzed.

G. Serum antibody response to L-PGA in mouse model. BALB/c mice (n=5, female, 6-8 weeks, Simonsen Laboratories, Inc., Gilroy, Calif.) were subcutaneously injected with the vaccine formulations as outlined in Table III.

| Vaccine | Lot Number | Protein Dose | Sigma Adjuvant/Dose | Injection Dose |
|---|---|---|---|---|
| Buffer | 080808A | 0 | 0 | 100 µl |
| L-CMI | 080808B | 0 | 0 | 100 µl |
| L-CMI + MPL | 080808C | 0 | MPL/15 µg | 100 µl |
| L-CMI + PGA | 080808D | 15 µg | 0 | 100 µl |
| L-CMI + MPL + PGA | 080808E | 15 µg | MPL/15 µg | 100 µl |
| PGA-BSA/Alum | | 25 µg | Alum/50 µg | 150 µl |

The vaccine formulations, except the PGA-BSA/Alum, were prepared as described in Table II. Mice were dosed on days 0, 14, 28, euthanized on day 52, and bled by cardiac puncture. The levels of anti-PGA in serum samples were determined using enzyme-linked immunosorbent assay (ELISA). Briefly, Pro-Bind™, flat bottom, polystyrene, 96-well plates (BD Biosciences, San Jose, Calif.) were coated with 100 ng of PGA dissolved in 100 µl carbonate buffer (0.1 M, pH 9.6) overnight at 4° C. The PGA used to coat the plates was previously purified from *Bacillus licheniformis* in Dr. Cui's lab in OSU. For anti-PGA measurement, plates were washed with PBS/Tween 20 (10 mM, pH 7.4, 0.05% Tween 20, Sigma-Aldrich) and blocked with 5% (v/v) horse serum in PBS/Tween 20 for 1 hr at 37° C. Samples were diluted 2-fold serially in 5% horse serum in PBS/Tween 20, added to the plates following removal of the blocking solution, and incubated for an additional 3-4 hr at 37° C. The serum samples were removed, and the plates were washed 5 times with PBS/Tween 20. Horse radish peroxidase (HRP)-labeled goat anti-mouse immunoglobulin (IgG, IgG1, IgG2a, or IgM, 5.000-fold dilution in 1.25% horse serum in PBS/Tween 20, Southern Biotechnology Associates, Inc. Birmingham, Ala.) was added into the plates, followed by another 1 hr incubation at 37° C. Plates were again washed 5 times with PBS/Tween 20. The presence of bound Ab was detected following a 30 min incubation at room temperature in the presence of 3,3', 5,5'-Tetramethylbenzidine substrate (TMB, Sigma-Aldrich), followed by the addition of 0.2 N sulfuric acid as the stop solution. The absorbance was read at 450 nm using a BioTek Synergy HT Multi-Detection Microplate Reader (BioTek Instruments, Inc. Winooski, Vt.).

G. Preparation of *B. licheniformis* spore suspension. Spore suspension of *B. licheniformis* was prepared as described elsewhere (Feijo et al., 1997). Briefly, *B. licheniformis* cultures were shaken at 37° C., 250 rpm for 36-48 hr and inoculated on LB agar plates. The plates were incubated for 5 days at 37° C. to encourage sporulation. Spores from each plate were collected after the addition of 5 mL of sterile, ice-cold de-ionized water to the plate surface, followed by removal with a sterile scraper. The spore suspensions were washed 10 times successively with ice-cold de-ionized water, followed by centrifugation at 10,000×g for 20 min. Between washings, the supernatant was decanted, and the pellets were re-suspended in sterile, ice-cold de-ionized water. After the final wash, spores were re-suspended in PBS (pH 7.0, 10 mM) and heated for 12 min at 80° C. to kill any remaining vegetative bacteria. The spore suspension was immediately cooled in an ice-water bath and then stored at 4° C. until further use.

H. Complement-mediated bacteriolysis assay. *B. licheniformis* spores were re-suspended in LB broth and incubated at 37° C. for 90 min without shaking. The freshly germinated vegetative *bacillus* cells were centrifuged for 5 min at 14,000 rpm, and re-suspended in LB broth to a concentration of ~450 CFU in 60 µL. Serum samples from individual mice were pooled, heat-inactivated (56° C., 30 min), and diluted 10-fold serially in PBS. The assay condition was consisted of 60 µL of *bacillus* cell suspension, 20 µL of heat-inactivated serum, and 20 µL of rabbit complement (Sigma, diluted 1:4 in PBS). The mixture was incubated at 37° C. for 1 hr without shaking. Samples from each incubation mixture (30 µL) were plated on LB agar plates, and the plates were incubated for 8 hr at 37° C. The number of colonies formed was determined. As controls, bacteria were incubated with rabbit complement alone before being plated onto the LB agar plates. The percent of killed bacterial cells was calculated for each serum dilution by comparing with the number of colonies formed when the bacteria were incubated with complement alone.

I. Results & Discussion

Figure 2:
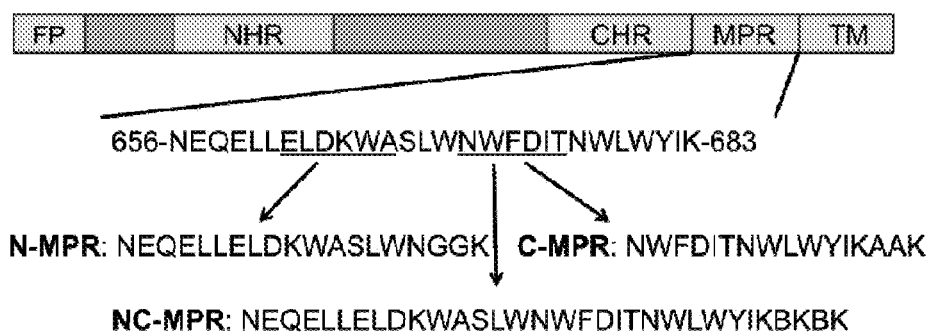
FIG. 2 depicts HIV-1 MPR epitopes N-MPR and C-MPR.

The lipid contents of liposomes formed were analyzed by HPLC. DMPG, DMPC, and cholesterol maintained their relative area ratio (approximately 0.12:0.68:1) throughout the liposome formation process, indicating stability and no significant specific loss of these components from processing. MPL contents were not analyzed due to the lack of an analytical method that can detect the low concentrations of MPL in these liposomes. Analysis of CMI contents showed distinct differences between L-CMI without (FIG. 2A) and with MPL (FIG. 2B); the area ratio of CMI to cholesterol are 1.83:1 and 0.95:1 respectively. Note that the initial CMI:cholesterol ratio before processing was approximately 2:1, indicating major depletion of CMI in both types of liposome during the formation process. Overall, based on current understanding of the process, CMI depletion and difference between the two liposome types were due to instability and loss of CMI under slightly varied processing conditions.

The estimated CMI available on the outer surfaces of these liposomes were approximately 0.50 and 0.33 mg/ml for L-CMI (2×) without and with MPL respectively. In theory, this available CMI can conjugate up to 0.79 and 0.52 mg PGA per ml 1× liposome respectively. Note that L-CMI were formulated to contain 0.75 mg CMI on the outer surface per ml L-CMI (2×), able to conjugate up to 1.2 mg PGA per ml 1× liposome. Our aim was to conjugate L-CMI to PGA to form chol-maleimide-PGA liposomes (L-PGA) at 0.15 mg PGA/ml 1× liposome. The available CMI on the surface of these L-CMI were sufficient for this purpose.

Conjugation of PGA to L-CMI. Due to various limitations, including limited availability of PGA and the finding that solubilized PGA can rapidly oxidize (presumably) and become non-conjugatable, the actual conjugation reactions were slightly modified. A PGA sample estimated at approximately 1 mg total PGA per ml, of unknown active PGA, was prepared and conjugated to the L-CMI. CMI area data analysis suggested a loss of 0.053 and 0.052 mg/ml for L-CMI without and with MPL respectively, equivalent to approximately 0.193 and 0.188 mg PGA conjugated per ml 1× liposome. This was higher than the targeted 0.15 mg/ml concentration. The extent of conjugation, as measure by loss of CMI, was consistent between the two liposomes at approximately 0.19 mg PGA/ml. Excess PGA and/or degradation product(s) were filtered out by ultra-filtration. To provide the 0.15 mg PGA/ml 1× liposome for the immunological study, these samples were diluted to 0.15 mg/ml using the respective empty 1× liposomes.

Figure 3:
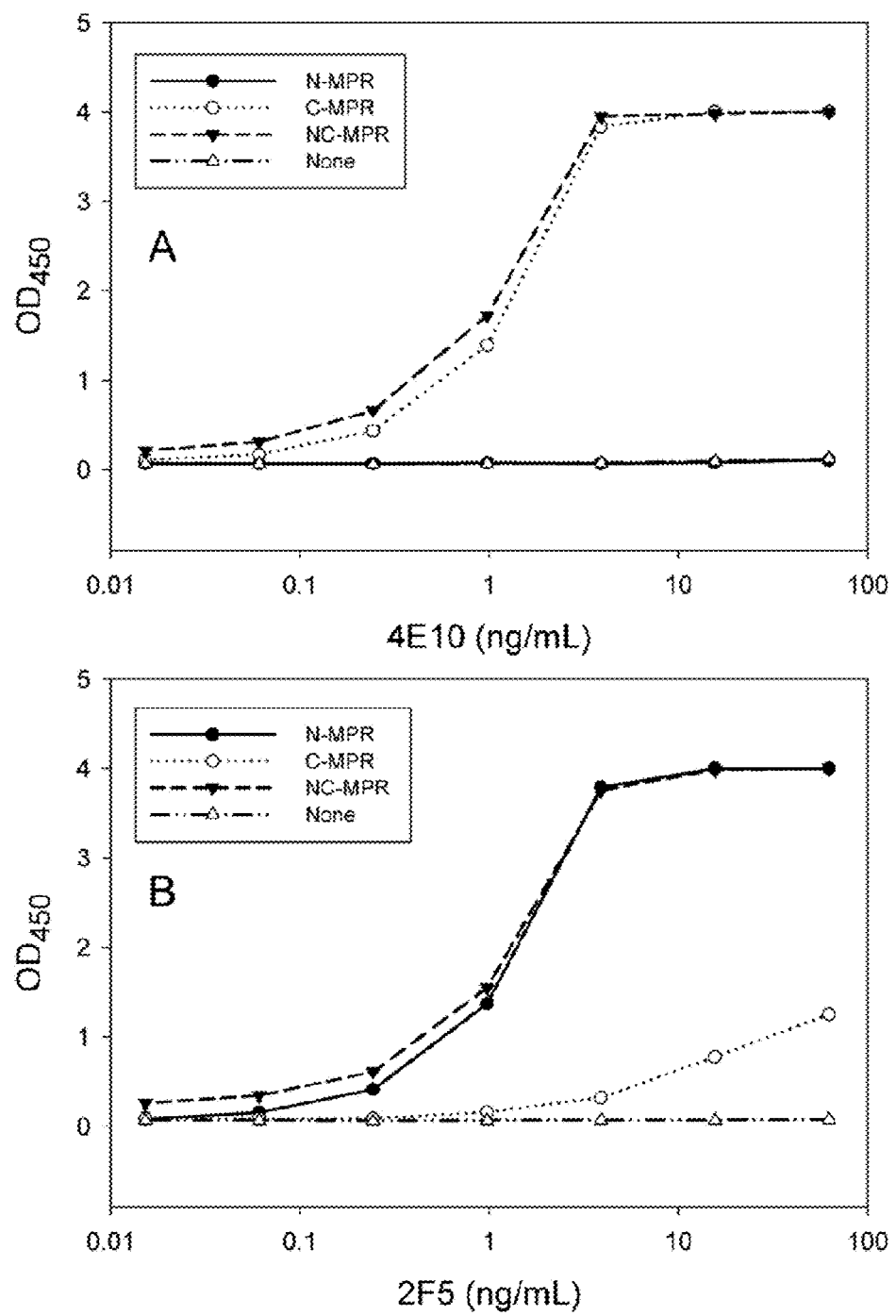
FIG. 3 depicts effects of the attached lipid moiety on MPR epitope secondary structure analysis.
Figure 4:
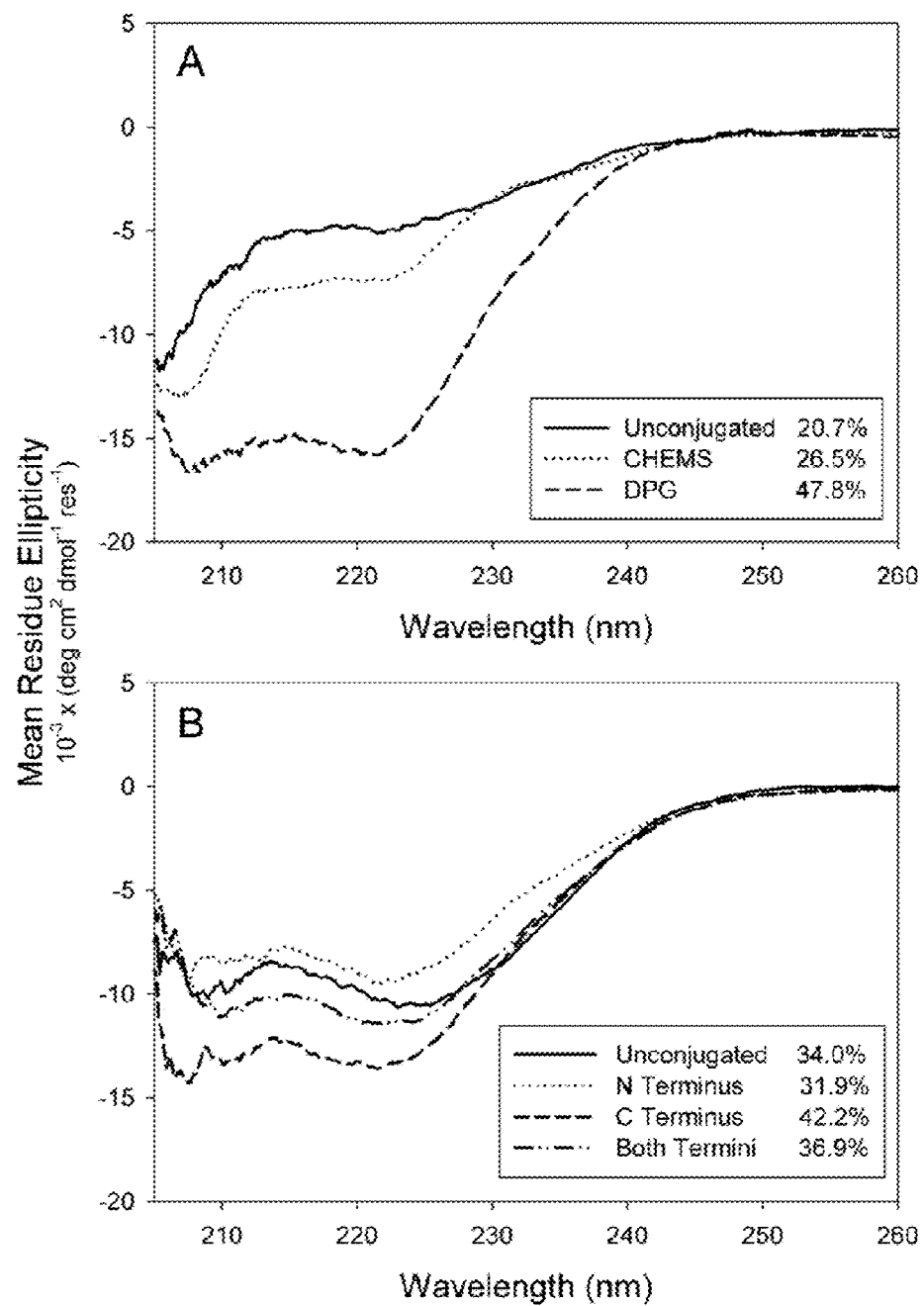
FIG. 4 depicts effects of the attached l ter conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ε-amino group of lysine reacts significantly with NHS-esters. A covalent amide bond is formed when the NHS-ester cross-linking agent reacts with primary amines, releasing N-hydroxysuccinimide.
Figure 5:
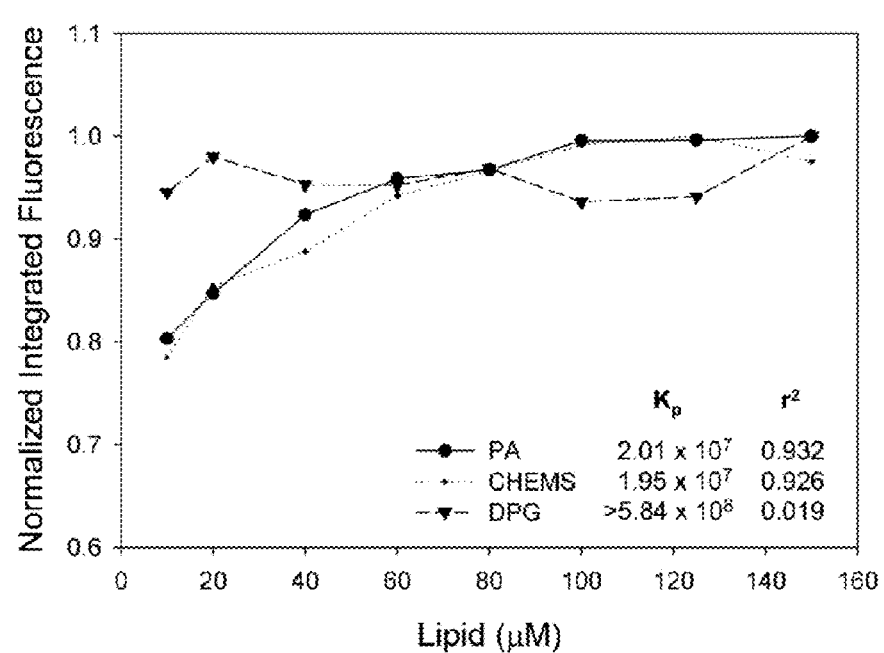
Figure 6:
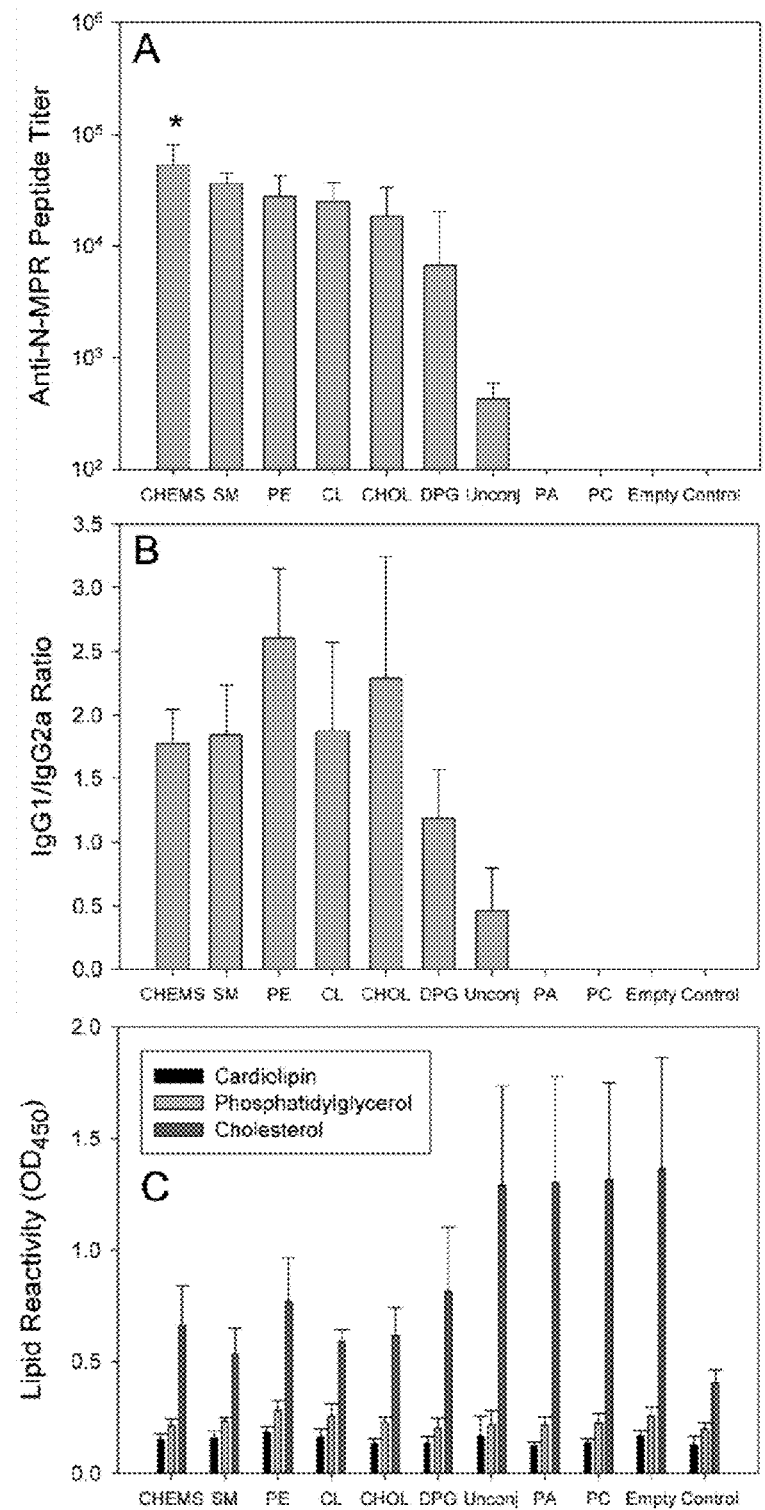
Figure 7:
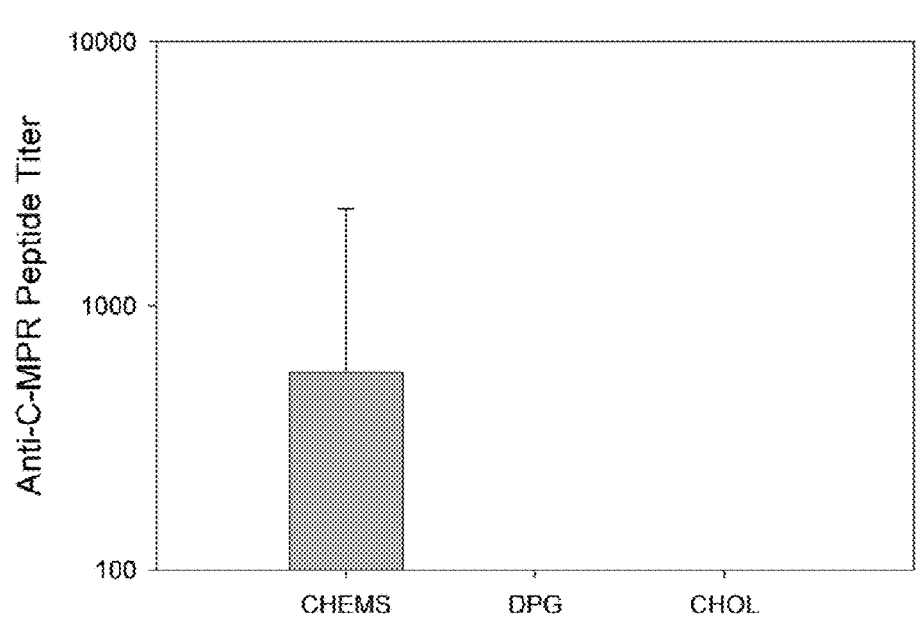

Freshly prepared PGA eluted at approximately 7.7 min as analyzed by HPLC (FIG. 3A). PGA preparations stored over time showed depletion of PGA at the 7.7 min peak with concomitant increase of a second peak at 16.4 min (FIG. 3B). When this older preparation was used to conjugate to L-CMI, only PGA was depleted while the degradation product remained constant, suggesting that the degradation product was not conjugatable. The degradation product has not been identified. It is presumed to be the oxidized (disulfide linked) dimeric form of PGA. Its non-conjugatability to L-CMI suggests that it does not contain free sulfhydryl groups, supporting the assumption of oxidation by disulfide bond formation.

The use of empty liposome to dilute the approximately 0.19 mg PGA/ml 1× liposome to the specification of 0.15 mg/ml for the immunological studies enabled the maintenance of lipid concentrations at 1× including MPL at 0.15 mg/ml and conjugated PGA at 0.15 mg/ml. Whether this non-homogenous mixture of empty liposome and 0.19 mg PGA/ml liposome has a significant effect (compare to ideal homogenous 0.15 mg/ml liposome) on immunological response is unknown.

Immunization with the L-CMI+MPL+PGA induced strong anti-PGA IgG and IgM Abs. The MPL adjuvant appears to be necessary to induce anti-PGA Abs, as evidenced by the lack of an anti-PGA IgG Ab response in the L-CMI+PGA group. Both anti-PGA IgG1 and IgG2a Abs were elicited in mice immunized with the L-CMI+MPL+PGA. As expected, immunization with L-CMI or L-CMI+MPL did not induce an anti-PGA Ab response.

*Bacillus*-killing activity of L-PGA vaccines. To evaluate the functionality of the anti-PGA Abs induced, a complement-mediated bactericidal assay was completed as described elsewhere with modifications (Chabot et al., 2004). Due to the biohazards associated with *B. anthracis*, *B. licheniformis* was used as a model system. It has been shown that the PGAs from *B. anthracis* and *B. licheniformis* were chemically and immunologically identical (Makino et al., 1989; Mesnage et al., 1998). Serum samples from mice subcutaneously immunized with L-CMI+MPL+PGA activated complement and had *bacillus*-killing activity comparable to that from mice subcutaneously immunized with PGA-BSA adsorbed onto Alum.

J. Conclusions

PGA was successfully conjugated onto L-CMI at 0.15 mg/ml without or with 0.15 mg/ml MPL to form anti-Bacillus vaccines. Mice vaccinated with L-PGA containing MPL showed induction of anti-PGA IgG and IgM Abs comparable to PGA-BSA/Alum vaccination. Serum from L-PGA+MPL vaccinated mice showed *bacillus*-killing activity as demonstrated by the complement-mediated bactericidal assay.

K. References

Chabot D J, Scorpio A, Tobery S A, Little S F, Norris S L, Friedlander A M. Anthrax capsule vaccine protects against experimental infection. Vaccine. 2004 Nov. 15; 23(1):43-7.

Feijoo S C, Hayes W W, Watson C E, Martin J H. Effects of Microfluidizer Technology on *Bacillus licheniformis* Spores in Ice Cream Mix. J Dairy Sci. 1997; 80(9):2184-7.

Makino S, Uchida I, Terakado N, Sasakawa C, Yoshikawa M. Molecular characterization and protein analysis of the cap region, which is essential for encapsulation in *Bacillus anthracis*. J. Bacteriol. 1989 February; 171(2):722-30.

Mesnage S, Tosi-Couture E, Gounon P, Mock M, Fouet A. The capsule and S-layer: two independent and yet compatible macromolecular structures in *Bacillus anthracis*. J. Bacteriol. 1998 January; 180(1):52-8.

EXAMPLE 5

Efficacy of L-CMI-M2eA1 Against Influenza H1N1 Challenge

M2 protein M2eA1 of influenza A (H1N1) virus was used as a model antigen to demonstrate the ability of the maleimide-derivatized sterol to serve as an antigen anchor in an influenza challenge assay.

Female 6-week-old BALB/c mice (Harlan Laboratories, Indianapolis, Ind., USA) were used in this study. Animals were caged 5 or 7 mice per cage. Animals were maintained in microisolator cages with standard rodent diet (Taklad Laboratory Rodent diet #2918 (18% protein), Harlan/Teklad, Madison, Wis.) and water ad libitum.

The vaccines were prepared substantially as described above for PGA antigen. Doses administered to the mice are listed in Table 1. Vaccines were administered subcutaneously on day 0 and intranasally (IN) on day 60*. The mice were sedated with 100 mg/kg Ketamine and 16 mg/kg Xylaxine prior to the IN boost to ensure uptake of the boost by the nares of the mice.

| Group | Vaccine | Protein dose | Sigma Adjuvant/Dose | Injection Dose (ml) *Prime | Injection Dose (ml)* Boost |
|---|---|---|---|---|---|
| 1 | L-CMI | None | None | 0.10 | 0.05 |
| 2 | L-CMI | None | MPL 15 ug/dose | 0.10 | 0.05 |
| 3 | L-CMI | None | MPL 4.5 ug/dose | 0.10 | 0.05 |
| 4 | L-CMI-M2eA1 | 15 ug | None | 0.10 | 0.05 |
| 5 | L-CMI-M2eA1 | 15 ug | MPL 15 ug/dose | 0.10 | 0.05 |
| 6 | L-CMI-M2eA1 | 15 ug | MPL 4.5 ug/dose | 0.10 | 0.05 |
| 7 | L-M2eA1-HD | 15 ug | MPL 15 ug/dose | 0.10 | 0.05 |
| 8 | L-Control | None | MPL 15 ug/dose | 0.05 | 0.05 |
| 9 | Buffer | None | None | 0.10 | 0.05 |

Figure 9:
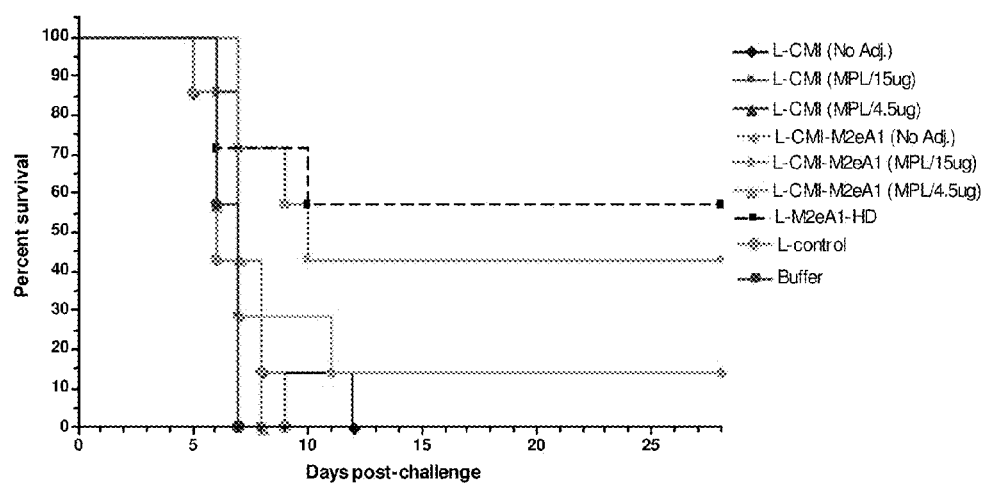

Mice were infected IN with 10 $LD_{50}H1N1$ (PR8) on day 67. IN infection required sedation of the mice with 100 mg/kg Ketamine and 16 mg/kg Xylazine. Mice immunized with L-M2eA1 (57.14% survival) were significantly protected against challenge with 10LD50H1N1 compared to mice administered Buffer, L-Control, L-CMI-M2eA1-MPL/4.5 ug, L-CMI-MPL/4.5 ug, L-CMI-MPL/15 ug, L-CMI-No Adj (0% survival, p<0.05) (FIG. 9).

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A composition comprising one or more immunogenic polypeptides of interest, the composition comprising:
   a) an aqueous vehicle;
   b) liposomes comprising
      (i) dimyristoylphosphatidylcholine ("DMPC"),
      (ii) one or more lipids selected from the group consisting of dimyristoylphosphatidylglycerol ("DMPG"), and dimyristoyltrimethylammonium propane ("DMTAP"), and
      (iii) at least one sterol derivative,
      at relative percentages of 50%-98% (i): 1%-25% (ii): 1%-25% (iii); and
   c) said one or more immunogenic polypeptide(s) covalently linked to between 1% and 100% of said at least one sterol derivative.

2. A composition according to claim 1, wherein said relative percentages are 70%-85% (i): 5%-15% (ii): 10%-15% (iii).

3. A composition according to claim 1, wherein said relative percentages are about 75% (i), about 10% (ii), and about 15% (iii).

4. A composition according to claim 1, wherein said sterol derivative has the following structure:

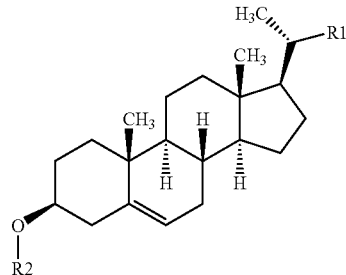

wherein:
one of R1 or R2 is a covalent linkage to said immunogenic polypeptide, wherein if R1 is said covalent linkage to said polypeptide, R2 is H, and if R2 is said covalent linkage to said immunogenic polypeptide, R1 is —CH$_2$—CH$_2$—CH$_2$—C(H)(CH$_3$)$_2$.

5. A composition according to claim 4, wherein R1 is —CH$_2$—CH$_2$—C(O)—X, wherein X is said immunogenic polypeptide, and R2 is H.

6. A composition according to claim 4, wherein R1 is —$CH_2$—$CH_2$—$CH_2$—$C(H)(CH_3)_2$, and R2 is —$C(O)$—$CH_2$—$CH_2$—$C(O)$—X, wherein X is said immunogenic polypeptide.

7. A composition according to claim 1, wherein said liposomes are substantially between 50 and 500 nm in diameter.

8. A composition according to claim 7, wherein said liposomes are substantially between 50 and 200 nm in diameter.

9. A composition according to claim 7, wherein said liposomes are substantially between 50 and 150 nm in diameter.

10. A composition according to claim 1, wherein said one or more immunogenic polypeptide(s) are covalently linked to between about 5% and about 10% of said at least one sterol derivative.

11. A composition according to claim 1, wherein said liposomes further comprise one or more components selected from the group consisting of monophosphoryl lipid A, resiquimod, flagellin, CpG, and α-galactosylceramide.

12. A composition according to claim 1, wherein at least one of said immunogenic polypeptide(s) are covalently linked to said one or more sterol derivatives through a lysine residue on said immunogenic polypeptide(s).

13. A composition according to claim 1, wherein at least one of said immunogenic polypeptide(s) are covalently linked to said one or more sterol derivatives through a cysteine residue on said immunogenic polypeptide(s).

14. A composition according to claim 1, wherein at least one of said immunogenic polypeptide(s) are covalently linked to said one or more sterol derivatives through a aspartate or glutamate residue on said immunogenic polypeptide(s).

15. A composition according to claim 1, wherein at least one of said immunogenic polypeptide(s) are covalently linked to said one or more sterol derivatives through a serine or threonine residue on said immunogenic polypeptide(s).

16. A composition according to claim 1, wherein at least one of said immunogenic polypeptide(s) are covalently linked to said one or more sterol derivatives through an N-terminal amine on said immunogenic polypeptide(s).

17. A composition according to claim 1, wherein at least one of said immunogenic polypeptide(s) are covalently linked to said one or more sterol derivatives through a C-terminal carboxyl on said immunogenic polypeptide(s).

18. A composition according to claim 1, wherein said covalent linkage to said immunogenic polypeptide comprises an (alkylene oxide)$_n$ moiety having an average length n of between 40 and 1000.

19. A composition according to claim 1, wherein said covalent linkage to said immunogenic polypeptide has the structure —R3-X, wherein:

R3 is $C_{0-12}$ straight or branched chain alkyl, or $C_{0-6}$ straight or branched chain alkyl-(alkylene oxide)$_n$—$C_{0-6}$ straight or branched chain alkyl, wherein n is on average between 40 and 1000;

each said straight or branched chain alkyl optionally comprises from 1-3 chain heteroatoms and one or more substituents independently selected from the group consisting of halogen, trihalomethyl, —$C_{1-6}$ alkoxy, —$NO_2$, —$NH_2$, —OH, —CH2OH, —CONH2, and —C(O)(OR4) where R4 is H or $C_{1-3}$ alkyl; and X is said immunogenic polypeptide.

20. A composition according to claim 1, wherein the lipid in (ii) is DMPG.

21. A composition according to claim 1, wherein said sterol derivative(s) is/are derivative(s) of cholesterol, cholesteryl chloroformate, stigmasterol, sitosterol, ergosterol, lanosterol, desmosterol, or campesterol.

\* \* \* \* \*